(12) United States Patent
Zhang et al.

(10) Patent No.: US 10,466,371 B2
(45) Date of Patent: Nov. 5, 2019

(54) APPARATUS AND METHODS FOR DEPTH-OF-INTERACTION POSITRON TOMOGRAPHY DETECTOR USING DICHOTOMOUS SENSING

(71) Applicant: Board of Regents, The University of Texas System, Austin, TX (US)

(72) Inventors: Yuxuan Zhang, Pearland, TX (US); Wai-hoi Wong, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 15/570,724

(22) PCT Filed: Apr. 29, 2016

(86) PCT No.: PCT/US2016/029922
§ 371 (c)(1),
(2) Date: Oct. 30, 2017

(87) PCT Pub. No.: WO2016/178933
PCT Pub. Date: Nov. 10, 2016

(65) Prior Publication Data
US 2018/0292548 A1 Oct. 11, 2018

Related U.S. Application Data

(60) Provisional application No. 62/155,695, filed on May 1, 2015.

(51) Int. Cl.
| | | |
|---|---|---|
| *G01T 1/29* | (2006.01) | |
| *G01T 1/202* | (2006.01) | |
| *G01T 1/20* | (2006.01) | |
| *A61B 6/03* | (2006.01) | |

(52) U.S. Cl.
CPC ............ *G01T 1/2985* (2013.01); *A61B 6/037* (2013.01); *G01T 1/2002* (2013.01); *G01T 1/202* (2013.01)

(58) Field of Classification Search
CPC ....... A61B 6/037; G01T 1/2985; G01T 1/202; G01T 1/2002
USPC .............. 250/363.03, 366, 362, 363.04, 367, 250/370.11
See application file for complete search history.

(56) References Cited

U.S. PATENT DOCUMENTS

| | | | |
|---|---|---|---|
| 3,594,577 A * | 7/1971 | Loveday | G01T 1/1644 |
| | | | 250/363.02 |
| 5,329,124 A * | 7/1994 | Yamamoto | G01T 1/2002 |
| | | | 250/366 |
| 6,087,656 A | 7/2000 | Kimmich et al. | |
| 7,696,481 B2 | 4/2010 | Tkaczyk | |
| 7,737,407 B2 | 6/2010 | Grazioso et al. | |
| 8,115,174 B2 | 2/2012 | Nelson | |

(Continued)

OTHER PUBLICATIONS

International Preliminary Report on Patentability issued in corresponding PCT Application No. PCT/US16/29922, dated Nov. 7, 2017.

(Continued)

*Primary Examiner* — Marcus H Taningco
*Assistant Examiner* — Blake C Riddick
(74) *Attorney, Agent, or Firm* — Parker Highlander PLLC

(57) ABSTRACT

Apparatus and methods for depth-of-interaction (DOI) positron tomography detection are disclosed herein. Certain embodiments utilize dichotomous sensing to obtain DOI information.

20 Claims, 20 Drawing Sheets

(56) References Cited

U.S. PATENT DOCUMENTS

| | | |
|---|---|---|
| 8,933,410 B2 | 1/2015 | Inadama et al. |
| 8,957,385 B2 | 2/2015 | Frank et al. |
| 2009/0032717 A1* | 2/2009 | Aykac ............... G01T 1/2018 250/367 |
| 2010/0172565 A1* | 7/2010 | Degenhardt ......... G01T 1/2985 382/131 |
| 2013/0153774 A1* | 6/2013 | Hughes ............... G01T 1/1644 250/366 |
| 2014/0110592 A1 | 4/2014 | Nelson et al. |
| 2015/0028218 A1 | 1/2015 | Kataoka et al. |
| 2015/0034829 A1 | 2/2015 | Koschan et al. |
| 2015/0323684 A1* | 11/2015 | Xie ..................... A61B 6/4258 250/486.1 |

OTHER PUBLICATIONS

International Search Report and Written Opinion issued in corresponding PCT Application No. PCT/US16/29922, dated Aug. 5, 2016.

Ito et al., "Positron Emission Tomography (PET) Detectors with Depth-of-Interaction (DOI) Capability," *Biomed. Eng. Lett.*, 1:70-81, 2011.

* cited by examiner

Anger

Light-channel

Geometrical Mean

Z = 2 mm

Z = 4 mm

Z = 6 mm

Z = 8 mm

Z = 10 mm

Sum of 5 depths

Anger

Light-Channel

Geometric mean

APPARATUS AND METHODS FOR DEPTH-OF-INTERACTION POSITRON TOMOGRAPHY DETECTOR USING DICHOTOMOUS SENSING

CROSS-REFERENCE TO RELATED APPLICATIONS

This application is a national phase application under 35 U.S.C. § 371 of International Application No. PCT/US2016/029922, filed Apr. 29, 2016, which claims priority to U.S. Provisional Patent Application Ser. No. 62/155,695 filed May 1, 2015, the entire contents of each of which are incorporated herein by reference.

BACKGROUND INFORMATION

Positron emission tomography (PET) can detect tumor in vivo based on the living chemistry of cancer tissues. In recent years, PET has well demonstrated its broad clinical utilities in cancer diagnosis and is recognized as an important tool to study cancer functions in vivo, because of its unique ability to elicit molecular functions. The in vivo molecular imaging ability of PET has triggered considerable cancer-research interest and radiotracer development to study cancer related molecular processes such as angiogenesis, apoptosis, cell proliferation, hypoxia, gene expression and blood flow.

Despite this success, the cancer-application potential of PET in whole body is still largely untapped today because of high scanner cost, and low image resolution. As of 2009, clinical PET cameras have imaging resolution of 4.0-6.3 mm, but because of low sensitivity, the practical clinical resolution is worse (7-10 mm), which can miss smaller (early) primary lesions and metastases. In the last decade, researchers have focused on the development of low-cost ultrahigh resolution PET technologies and PET cameras.

PET camera detectors are made up of tens of thousands of scintillation crystals and thousands of photosensors. The most commonly used photosensors in clinical PET cameras are photomultiplier tubes (PMT). Although other solid-state or semiconductor photosensors are also being investigated, such sensors are currently more expensive than PMT.

PET resolution progressively deteriorates from the center due to the depth-of-interaction (DOI) of gamma rays in the thick PET detectors. Secondly, clinical PET image quality suffers from insufficient signal counts. Signal deprivation in PET can typically be alleviated by: (i) increasing the detector depth, (ii) increasing the PET axial field-of-view, and (iii) decreasing the diameter of the PET ring. However, these options cause even worse DOI resolution degradation. The lack of DOI information in clinical PET is due to the high cost of implementing DOI measurements in the large clinical systems. Embodiments disclosed herein include a lower-cost, ultrahigh-resolution DOI PET-detector design, which may provide higher spatial resolution and sensitivity than current commercial PET/MR (PET/CT) systems, while using even less silicon photomultipliers (SiPM) than do the non-DOI PET detectors in current clinical systems. Tens of thousands of costly SiPM and its supporting electronic channels are used to detect the scintillation light from each of the tens of thousands of scintillation-crystal detectors in a PET system. Thus it may enable practical ultrahigh-resolution, high-sensitivity clinical PET/MR and PET/CT with DOI to be realized with a lower production cost than the current clinical PET/MR and PET/CT systems without DOI.

SUMMARY

As explained in more detail below, exemplary embodiments of the present disclosure enable improvements in many aspects of PET detectors, including improved resolution, lower manufacturing costs, and reduced heat load during operation.

One robust way to measure DOI (Z) is to have two 2D SiPM arrays coupled to the top and the bottom sides of a scintillator array respectively. This traditional two-end readout design has significant information redundancy because both the top and bottom SiPM arrays capture the X and Y positions of the same firing scintillator. Exemplary embodiments disclosed herein can eliminate this redundancy by reading only the X position from the top of the crystal array with a 1-D SiPM array, and reading only the orthogonal Y position with a bottom 1-D SiPM array. Accordingly, one can reduce the two 2-D SiPM arrays to two 1-D arrays to read out the XY positions. The DOI position (Z) can still be derived from the difference between the top signal (X) and bottom signal (Y). Hence, in principle, exemplary embodiments can capture all XYZ (3-D) positions with just two 1-D SiPM arrays instead of two 2-D SiPM arrays, reducing the SiPM, heat and electronics complexity from $2 \times N^2$ to $2N$. This removal of information redundancy will significantly reduce the manufacturing cost of PET with DOI. Even in the conventional non-DOI PET design, a 2-D SiPM array ($N^2$) is needed to read the XY position. Following this minimum-redundancy notion, exemplary embodiments disclosed herein include dichotomous-orthogonal-symmetry detector (DOS) configurations. In addition, disclosed embodiments include embodiments with planar arrays of detectors disposed at opposite ends of crystals.

Certain embodiments include an apparatus for optical emission detection, the apparatus comprising: a block comprising scintillation crystals configured in an arrangement having X-Y-Z dimensions; a first linear array of light sensors coupled to a column of scintillation crystals parallel to the X-dimension; a second linear array of light sensors coupled to a row of scintillation crystals parallel to the Y-dimension, wherein the second linear array of light sensors is spaced apart from the first linear array of light sensors in the Z-dimension; and reflecting film coupled to a plurality of scintillation crystals of the block. In particular embodiments, a first portion of the reflecting film is coupled to each side of a first plurality scintillation crystals, where the first portion of the reflecting film is parallel to the first linear array of light sensors; a second portion of the reflecting film is coupled to each side of a second plurality scintillation crystals, where the second portion of the reflecting film is parallel to the second array of light sensors; and the first portion of the reflecting film is offset from the second portion of the reflecting film in the Z-dimension.

In specific embodiments, the first linear array of light sensors is coupled to a first end of the block; the second linear array of light sensors is coupled to a second end of the block; the first portion of the reflecting film is not coupled to the first end of the block; and the second portion of the reflecting film is not coupled to the second end of the block. In some embodiments, the first portion of the reflecting film is not coupled to any scintillation crystals on a plane of scintillation crystals comprising the column of scintillation crystals to which the first linear array of light sensors is coupled; and the second portion of the reflecting film is not coupled to any scintillation crystals on a plane of scintillation crystals comprising the row of scintillation crystals to which the second linear array of light sensors is coupled.

Certain embodiments further comprise: a third linear array of light sensors coupled to a second column of scintillation crystals of the scintillation crystal block, where the third linear array of light sensors is parallel to the first linear array of light sensors; and a fourth linear array of light sensors coupled a second row of scintillation crystals of the scintillation crystal block, where the fourth linear array of light sensors is parallel to the second linear array of light sensors. In particular embodiments, the first portion of the reflecting film comprises a first plurality of openings; and the second portion of the reflecting film comprises a second plurality of openings. In some embodiments, the first portion of reflecting film forms a first plurality of channels for light transmission across columns of scintillation crystals at a first end of the block; the second portion of reflecting film forms a plurality of channels for light transmission across rows of scintillation crystals at a second end of the block; the first plurality of openings is configured to allow light to be distributed between the first plurality of channels for light transmission; and the second plurality of openings is configured to allow light to be distributed between the second plurality of channels for light transmission. In specific embodiments, the first and second linear arrays of light sensors comprise silicon photomultipliers.

In certain embodiments, the block comprises segmented scintillation crystals segmented into several sections and optically glued back together; and the segmented scintillation crystals increase the impedance of light and provide a larger signal difference in light received by a sensor in the first linear array of light sensors and a sensor in the second linear array of light sensors.

Particular embodiments include an apparatus configured as positron emission detector, the apparatus comprising: a block comprising scintillation crystals configured in an arrangement having X-Y-Z dimensions; reflecting film coupled to the scintillation crystals; a first non-planar array of light sensors coupled to a first plurality scintillation crystals; a second non-planar array of light sensors coupled to a second plurality scintillation crystals; and a processor configured to analyze data from the first and second non-planar array of light sensors, where: the processor is configured to calculate the X-Y-Z dimensions of a scintillation crystal emitting light detected by both a first light sensor in the first non-planar array of light sensors and by a second light sensor in the second non-planar array of light sensors. In some embodiments, the first and second non-planar arrays of light sensors are orthogonal to each other. In specific embodiments, the first non-planar array of light sensors is coupled to a column of scintillation crystals; and the first non-planar array of light sensors is coupled to a row of scintillation crystals.

In certain embodiments, a first portion of the reflecting film is not coupled to the column of scintillation crystals to which the first non-planar array of light sensors is coupled, and a second portion of the reflecting film is not coupled to the row of scintillation crystals to which the second non-planar array of light sensors is coupled. In particular embodiments, the first portion of the reflecting film is not coupled to any scintillation crystals on a plane of scintillation crystals comprising the row of scintillation crystals to which the first non-planar array of light sensors is coupled; and the second portion of the reflecting film is not coupled to any scintillation crystals on a plane of scintillation crystals comprising the column of scintillation crystals to which the second non-planar array of light sensors is coupled. Some embodiments further comprise: a third non-planar array of light sensors coupled to a second row of scintillation crystals of the block, where the third linear array of light sensors is parallel to the first non-planar array of light sensors; and a fourth non-planar array of light sensors coupled a second column of scintillation crystals of the block, where the fourth linear array of light sensors is parallel to the second non-planar array of light sensors. In specific embodiments, the first portion of the reflecting film comprises a first plurality of openings, and the second portion of the reflecting film comprises a second plurality of openings.

In certain embodiments, the first plurality of openings is configured to allow light to traverse between two channels to reach the closest neighboring sensors in the first non-planar array of light sensors, and the second plurality of openings is configured to allow light to traverse between two channels to reach the closest neighboring sensors in the second non-planar array of light sensors. In particular embodiments, the first and second linear arrays of light sensors comprise silicon photomultipliers.

Some embodiments include an apparatus configured as positron emission detector, the apparatus comprising: a block having X-Y-Z dimensions comprising scintillation crystals having a first end and a second end; a first plurality of light sensors in the X-Y plane coupled to the first end of the scintillation crystals; a second plurality of light sensors in the X-Y plane coupled to the second end of the scintillation crystals, where: an X-Y location of a signal emitted by a scintillation crystal is determined by an X-Y location of a first sensor in the first plurality of sensors that detects the signal and by an X-Y location of a second sensor in the second plurality of sensors that detects the signal; and a Z-location of the signal is determined by a difference in signal intensities detected by the first sensor and the second sensor.

Specific embodiments further comprise a processor configured to determine the X-Y location and the Z-location of the signal. In certain embodiments, each light sensor in the first plurality of light sensors is coupled to a plurality of adjacent scintillation crystals; and each light sensor in the second plurality of light sensors is coupled to a plurality of adjacent scintillation crystals. In certain embodiments, each scintillation crystal comprises X-Y dimensions less than X-Y dimensions for each light sensor in the first and second pluralities of light sensors. In particular embodiments, each scintillation crystal comprises X-Y dimensions equal to X-Y dimensions for each light sensor in the first and second pluralities of light sensors. In some embodiments, a center of each light sensor in the first plurality of sensors is offset diagonally from a center of each light sensor in the second plurality of light sensors. In specific embodiments, the block comprises segmented scintillation crystals segmented into several sections and optically glued back together, and the segmented scintillation crystals increase the impedance of light and provide a larger signal difference in light received by a sensor in the first plurality of light sensors and a sensor in the second plurality of light sensors.

Certain embodiments include an apparatus configured as positron emission detector, where the apparatus comprises: a block comprising scintillation crystals comprising a first end and a second end; reflective film coupled to the scintillation crystals; a first plurality of light sensors coupled to the first end of the scintillation crystals; and a second plurality of light sensors coupled to the second end of the scintillation crystals. In particular embodiments, the first plurality of light sensors comprises individual light sensors coupled to adjacent scintillation crystals in the block; the second plurality of light sensors comprises individual light sensors coupled to adjacent scintillation crystals in the block; and an individual scintillation crystal in the block is coupled to no more than one individual light sensor in the first plurality of light sensors and no more than one individual light sensor in the second plurality of light sensors.

In some embodiments, the individual light sensors in the first plurality of light sensors are coupled to at least four adjacent scintillation crystals in the block; and the individual light sensors in the second plurality of light sensors are coupled to at least four adjacent scintillation crystals in the block. In specific embodiments, the block comprises X-Y-Z dimensions; the first plurality of light sensors and the second plurality of sensors are arranged in an X-Y plane; an X-Y location of a signal emitted by a scintillation crystal is determined by an X-Y location of a first sensor in the first plurality of sensors that detects the signal and by an X-Y location of a second sensor in the second plurality of sensors that detects the signal; and a Z-location of the signal is determined by a difference in signal intensities detected by the first sensor and the second sensor.

In certain embodiments, the block comprises segmented scintillation crystals segmented into several sections and optically glued back together; and the segmented scintillation crystals increase the impedance of light and provide a larger signal difference in light received by a sensor in the first plurality of light sensors and a sensor in the second plurality of light sensors.

Particular embodiments include a method of detecting an X-Y-Z location of a scintillating crystal in a crystal block, the method comprising: obtaining a first set X and Y coordinates for a first sensor that detects light from the scintillating crystal; obtaining a second set of X and Y coordinates for a second sensor that detects light from the scintillating crystal; determining an X coordinate and a Y coordinate of the scintillating crystal based on first set X and Y coordinates and the second set of X and Y coordinates; and determining a Z coordinate of the scintillating crystal based on the amount of light detected by the first sensor and the second sensor. In some embodiments, the first sensor is arranged in a first linear array of sensors; the second sensor is arranged in a second linear array of sensors; and the first linear array is orthogonal to the second linear array.

In specific embodiments, the first sensor is arranged in a first planar array of sensors; the second sensor is arranged in a second planar array of sensors; the first planar array is coupled to a first end of the crystal block; and the second planar array is coupled to a second end of the crystal block.

In the following, the term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The terms "about", "substantially" and "approximately" mean, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will be apparent to those skilled in the art from this detailed description.

DETAILED DESCRIPTION OF ILLUSTRATIVE EMBODIMENTS

Figure 1:
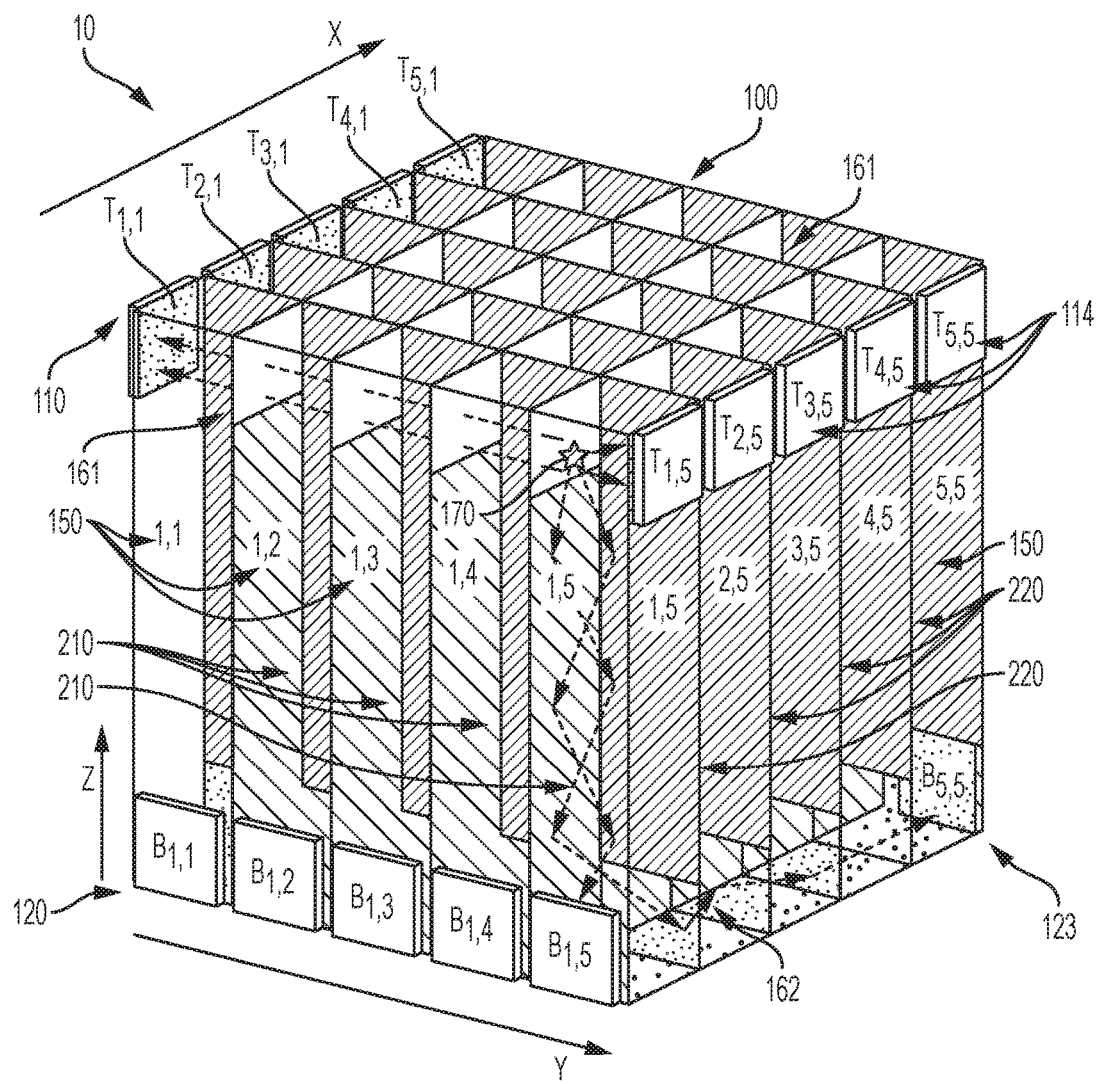
FIG. 1 displays a perspective view of an apparatus according to exemplary embodiments of the present disclosure.

Referring initially to FIG. 1, an apparatus 10 for optical emission detection comprises a block 100 comprising scintillation crystals 150 configured in an arrangement having X-Y-Z dimensions. It is understood that the use of X-Y-Z nomenclature (and other related terms such as "row" and "column") is used to refer to orthogonal axes, and is not intended to indicate any specific orientation for a particular dimension or axis. In addition, any reference to directions such as "top", "bottom", "left", "right", "front" or "back" is used for sake of convenience when referring to the figures disclosed herein, and is not intended to denote a particular location or orientation for all exemplary embodiments. In the embodiment shown in FIG. 1, block 100 comprises a 5×5 array of crystals. The location of an individual crystal is denoted in the figure by the X-Y coordinates. For example crystal 1,1 is located at row 1, column 1, while crystal 5,1 is located at row 5, column 1 and crystal 5,5 is located at row 5, column 5.

In the embodiment shown, block 100 comprises a first linear array of light sensors 110 coupled to a column of scintillation crystals, and a second linear array of light sensors 120 coupled to a row of scintillation crystals. In this particular embodiment, light sensors 110 are coupled to scintillation crystals in column 1 and light sensors 120 are coupled to scintillation crystals in row 1. As shown in FIG. 1, second linear array of light sensors 120 is spaced apart from first linear array of light sensors 110 in the Z-dimension. In particular embodiments, light sensors 110 and 120 may be configured as silicon photomultipliers (SiPMs).

In certain embodiments apparatus 10 may also comprise a third linear array of light sensors 114 coupled to a second column of scintillation crystals of the scintillation crystal block, and a fourth linear array of light sensors 123 coupled a second row of scintillation crystals of the scintillation crystal block. In the embodiment shown in FIG. 1, light sensors 114 are coupled to scintillation crystals in column 5 and light sensors 123 are coupled to scintillation crystals in row 5. As shown in FIG. 1, third linear array of light sensors 114 is parallel to first linear array of light sensors 110, and fourth linear array of light sensors 123 is parallel to second linear array of light sensors 120.

In addition, the embodiment shown also comprises reflecting film coupled to a plurality of scintillation crystals 150 of block 100. In this particular embodiment, a first portion 210 of the reflecting film is coupled to each side of a first plurality of scintillation crystals 150. First portion 210 of the reflecting film is oriented parallel to first linear array of sensors 110 (e.g. parallel to the X-dimension). The embodiment shown also comprises a second portion 220 of the reflecting film coupled to each side of a second plurality of scintillation crystals 150. Second portion 220 of the reflecting film is oriented parallel to second linear array of sensors 120 (e.g. parallel to the Y-dimension). Accordingly, second portion 220 of the reflecting film is oriented orthogonal to first portion 210 of the reflecting film.

In FIG. 1, reflecting film first portion 210 is shown in a lighter gray color, while reflecting film second portion 220 is shown in a darker gray color. As shown in FIG. 1, first portion 210 is offset from second portion 220 in the Z-dimension. For example, first portion 210 extends to the bottom of block 100, but does not extend to the top of block 100. Second portion 220 extends to the top of block 100, but does not extend to the bottom of block 100. This configuration provides for a plurality of channels 161 for light transmission across columns of scintillation crystals at the top of block 100 and for a plurality of channels 162 for light transmission across rows of scintillation crystals at the bottom of block 100. In certain embodiments, the crystals in the array are optically coupled (e.g. glued) together with an optically-transparent glue, so that light can pass across different columns (rows) in the no-reflector region on the top (bottom). Hence, light on top and light at the bottom are channeled orthogonally.

Exemplary embodiments can reduce processing requirements by detecting only the X position of a scintillating crystal 170 from the sum signal of $T_{11}$ of the first linear array 110 and $T_{15}$ of the third linear array 114, and detecting only the orthogonal Y position from the sum signal of $B_{15}$ of the second linear array 120 and $B_{55}$ of the fourth linear array 123. Thus one can reduce the two two-dimensional (e.g. planar) sensor arrays found on typical detectors to two one-dimensional (e.g. linear) arrays to determine the X-Y positions. The depth-of-interaction (DOI), e.g. the (Z) position can still be derived from the difference between the top signal (X) and bottom signal (Y). Hence, in principle, one can capture all XYZ (3-D) positions with just two 1-D sensor arrays instead of two 2-D sensor arrays, reducing the number of sensors, heat and electronics complexity from $2 \times N^2$ to $2N$. This removal of information redundancy will significantly reduce the manufacturing cost of PET with DOI. Even in the conventional non-DOI PET design, a 2-D SiPM array ($N^2$) is needed to read the XY position. Following this minimum-redundancy notion, exemplary embodiments disclosed herein include a novel Dichotomous-Orthogonal-Symmetry detector design (DOS).

The DOS design is shown in FIG. 1 with an N×N crystal array (N=5 is illustrated). In this embodiment, the crystal pixels are optically glued together. Reflecting mirror films cover four sides of each pixel but incompletely with open channels at each end in orthogonal directions. Those openings formed two sets of orthogonal channels (rows and columns) that light can pass through.

On the top end of the crystal array, a linear array of sensors $T_{ij}$ are coupled onto the two opposite ends of each row position to catch the light from each row of crystals (FIG. 1). On the bottom, sensors $B_{ij}$ are placed on the ends of each column position to catch the light from a column of crystals. For example, when the crystal pixel 170 at row 1, column 5 detects a gamma ray (indicate by the star in FIG. 1), the sum signal of sensor $T_{1,1}+T_{1,5}$ of row 1 will have the highest signal of all rows. Hence, the sum $T_{1,1}+T_{1,5}$ determines that a gamma has been detected in a crystal in row 1.

By the same token, on the bottom, the sum signal of $B_{1,1}+B_{1,5}$ will have the highest signal, which determines that the gamma ray has been detected in a crystal on column 5. Hence, the row and column position of the scintillating crystal $C_{1,5}$ can be determined. The crystal position is decoded by a simple binary-comparator instead of a complex analog-decoding circuit, thus simplifying electronics.

The DOI information (e.g. the Z-dimension) is derived from the difference of the sum of all top sensors and the sum of all bottom sensors, $$\text{DOI}=[\Sigma T_{i,j}-\Sigma B_{i,j}]/[\Sigma(T_{i,j}+B_{i,j})] \qquad (1)$$

where $\Sigma(T_{i,j}+B_{i,j})$ is the total energy. Hence, both the X-Y positions of the firing crystal and its DOI position (Z) can be derived. Two sensors for each row/column is also for improving light-collection uniformity. Advantages of this DOI-detector design include:

(a) For an N×N array, 4N sensors are needed, whereas in the conventional dual-end-readout DOI detector $2 \times N^2$ sensors are needed. Therefore, the cost of sensors and electronics of the new DOS block is 2/N that of the conventional DOI design; for N=10, the sensors and electronic cost is reduced by 80 percent.

(b) Even compared to the non-DOI detectors, the DOS DOI readout cost is 4/N the cost of the current non-DOI detectors.

Figure 2A:
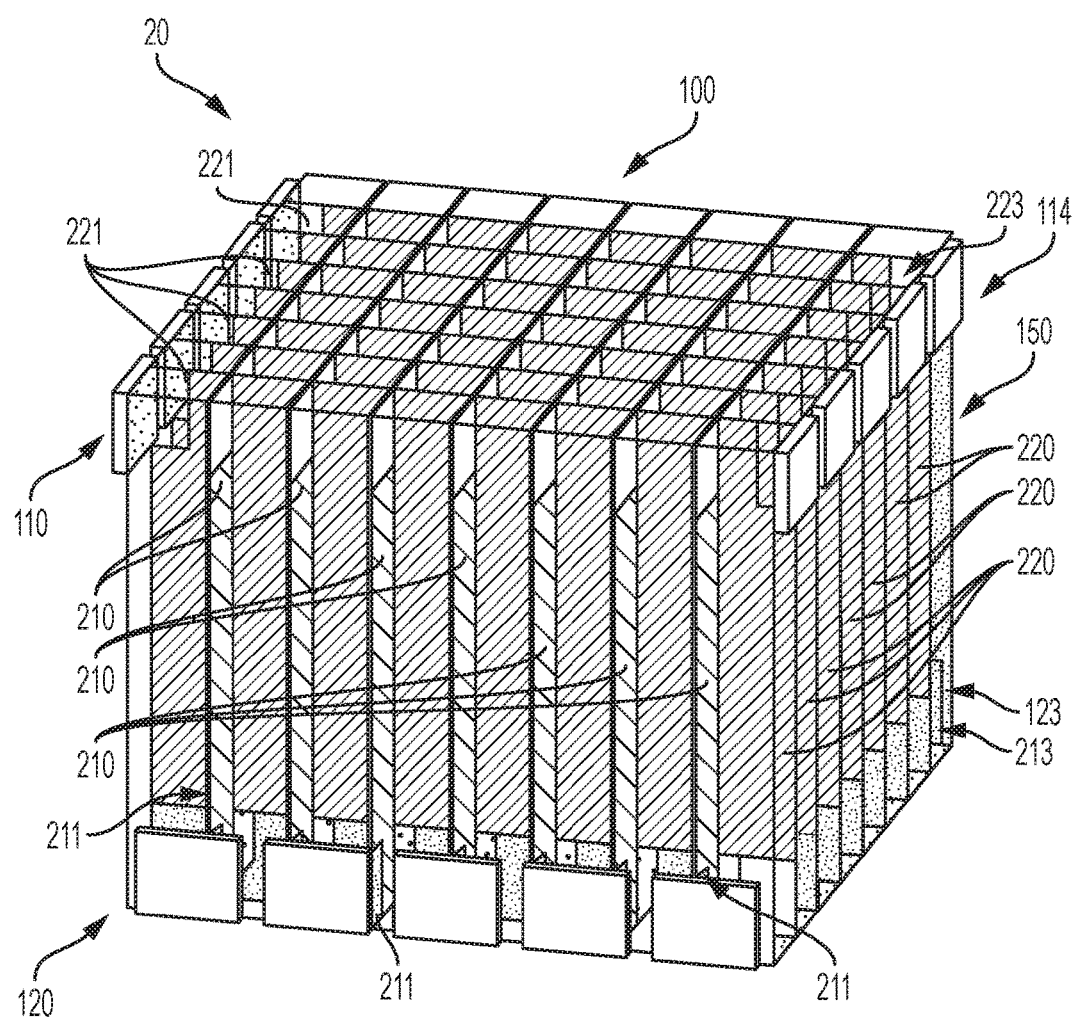
FIG. 2A displays a perspective view of an apparatus according to exemplary embodiments of the present disclosure.
Figure 2B:
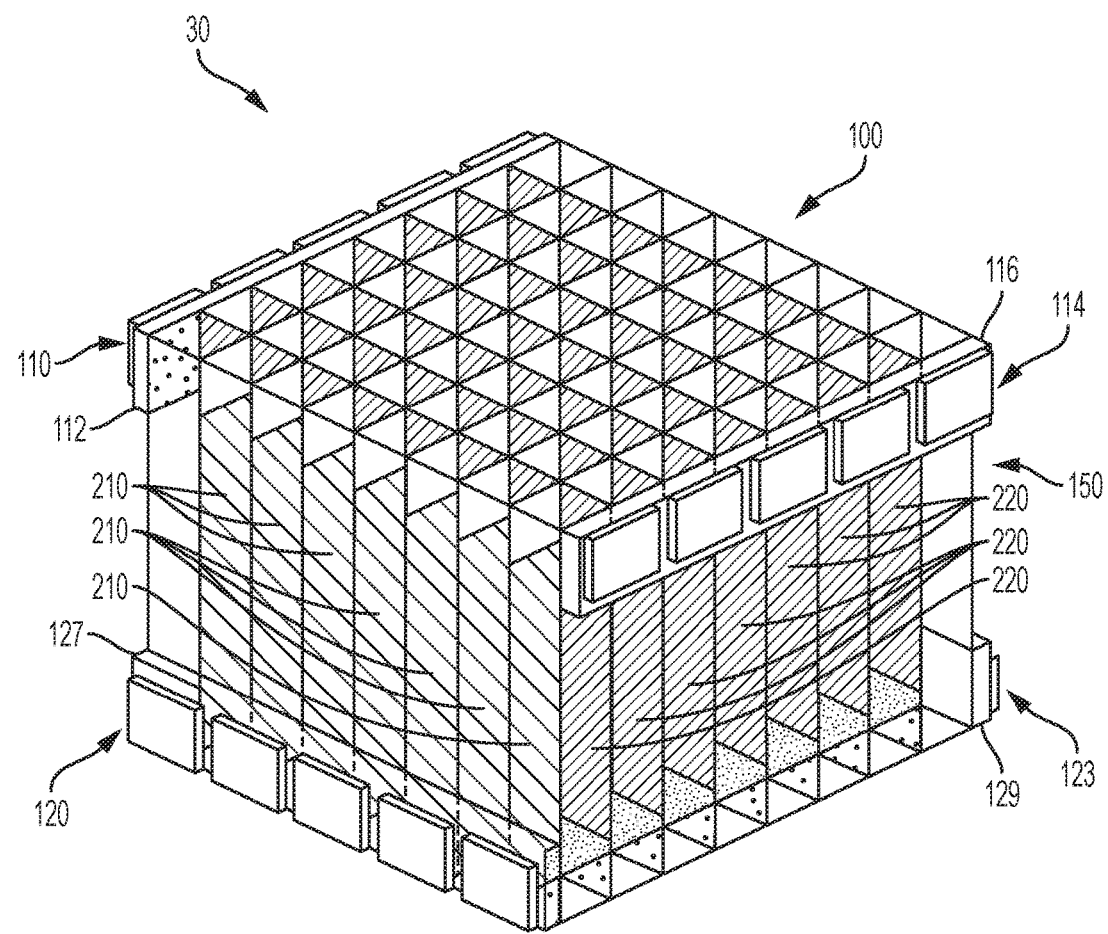
FIG. 2B displays a perspective view of an apparatus according to exemplary embodiments of the present disclosure.

Referring now to FIGS. 2A and 2B, additional embodiments comprise apparatus 20 and 30, respectively, that are similar to that shown in FIG. 1, but also provide the potential for higher spatial resolution. For purposes of clarity, not all features are labeled in the embodiments shown in FIGS. 2A and 2B, including in particular, features previously described in the embodiment shown in FIG. 1. For example, the X-Y-Z coordinates described in the previous embodiment is also used in this and following embodiments. In the embodiments shown, block 100 comprises an 8×8 array of crystals 150.

In the embodiment in FIG. 2A, reflecting film first portion 210 comprises a series of openings or openings 211 and 213 that provide additional channels for light to travel between and be shared by light sensors 120 and 123, respectively. In addition, reflecting film second portion 220 comprises a series of openings or openings 221 and 223 that provide channels for light to travel between and be shared by light sensors 110 and 114. Such a configuration can extend the DOS design to higher spatial resolution than the usual SiPM pitch of 3-4 mm by adding a path that allows light sharing between adjacent sensors.

The embodiment shown in FIG. 2B is similar to that shown in FIG. 2A. However the embodiment shown in FIG. 2B comprises a plurality of light guides (instead of channels in the reflective material) to allow for light to share between light sensors. In the embodiment shown, apparatus 30 comprises a light guide 112 coupled to block 100 and first linear array of light sensors 110, and a light guide 127 coupled to block 100 and second linear array of light sensors 120. In addition, apparatus 30 comprises a light guide 116 coupled to block 100 and third linear array of light sensors 114, and a light guide 129 coupled to fourth linear array of light sensors 123. During operation, light guides 112, 114, 127 and 129 function similar to the channels formed by openings 211, 213, 221 and 223 in the previously described embodiment in FIG. 2A. Accordingly, light guide 112 can allow for light to travel between and be shared by light sensors 110, while light guide 127 can allow light to travel between and be shared by light sensors 120. Similarly, light guide 116 can allow for light to travel between and be shared by light sensors 114, while light guide 129 can allow for light to travel between and be shared by light sensors 123.

In certain embodiments, the DOI resolution may be improved further if long crystal pixels are segmented into several sections (e.g. each several mm long) and then optically glued back together. In particular embodiments, the segmented length will vary depending on the optical properties of the crystals used and the surface roughness on the four cylindrical surfaces.

The segmentation increases the impedance of light going to the two ends, thus providing a larger signal difference received by the two sensors (e.g. SiPMs) at the opposite ends. The large signal difference as a function of depth will provide a higher DOI resolution.

Despite the unidirectional light channeling on each end, with configurations disclosed herein the top-end readout can provide both X and Y information; similarly, the bottom readout can also provide X and Y information. This bi-directional decoding from unidirectional light channeling at each end is enabled by the use of two symmetrically placed SiPMs on each channel.

1. Light-Channel decoding: the X-position can be calculated from just the bottom rows of sensors as (see FIG. 1 for notations). Exemplary embodiments of the present disclosure may comprise one or more computer processors configured to perform these and other calculations provided herein.

$$X_b = \left[\sum_{i=1}^{n}[(B_{1,i}+B_{2,i})*i] \Big/ \sum_{i=1}^{n}(B_{1,i}+B_{2,i}) - 1\right] \Big/ (n-1) \qquad (2)$$

2. Anger-Position Decoding: the X position can also be calculated by the classical Anger algorithm using the two summed energies from each side of the block. The same X-position described above can also be calculated from just the top layer of sensors by comparing the sum of the top sensors on the left side with the sum of the top sensors on the right sides in FIG. 1:

$$X_t = \frac{E_{right}}{E_{left}+E_{right}}, \left(\text{where } E_{right}=\sum_{i=1}^{n}T_{2,i}, E_{left}=\sum_{i=1}^{n}T_{1,i}\right) \qquad (3)$$

3. Composite Decoding: Moreover, since both bX and tX contain certain unique information about the X position, combining the two X decoding results would provide better (more robust) decoding as $X_c=f(X_b, X_t)$, where $f(X_b, X_t)$ is a smart weighting function (see FIGS. 4 and 5).

Simulation Data

Figure 3A:
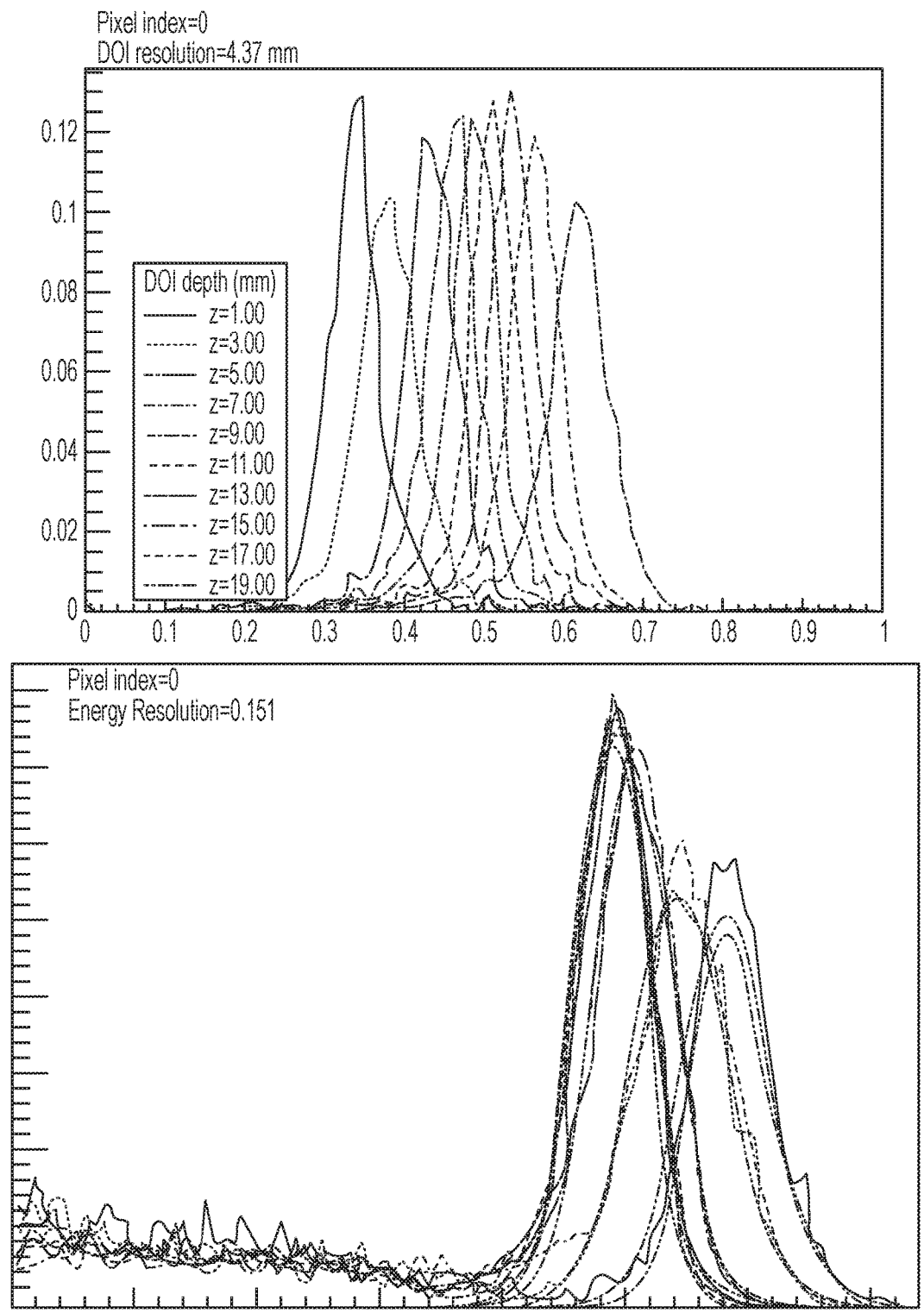
FIGS. 3A-3C display show point spread function and energy spectra of three selected pixel locations for an apparatus according to exemplary embodiments of the present disclosure.
Figure 3B:
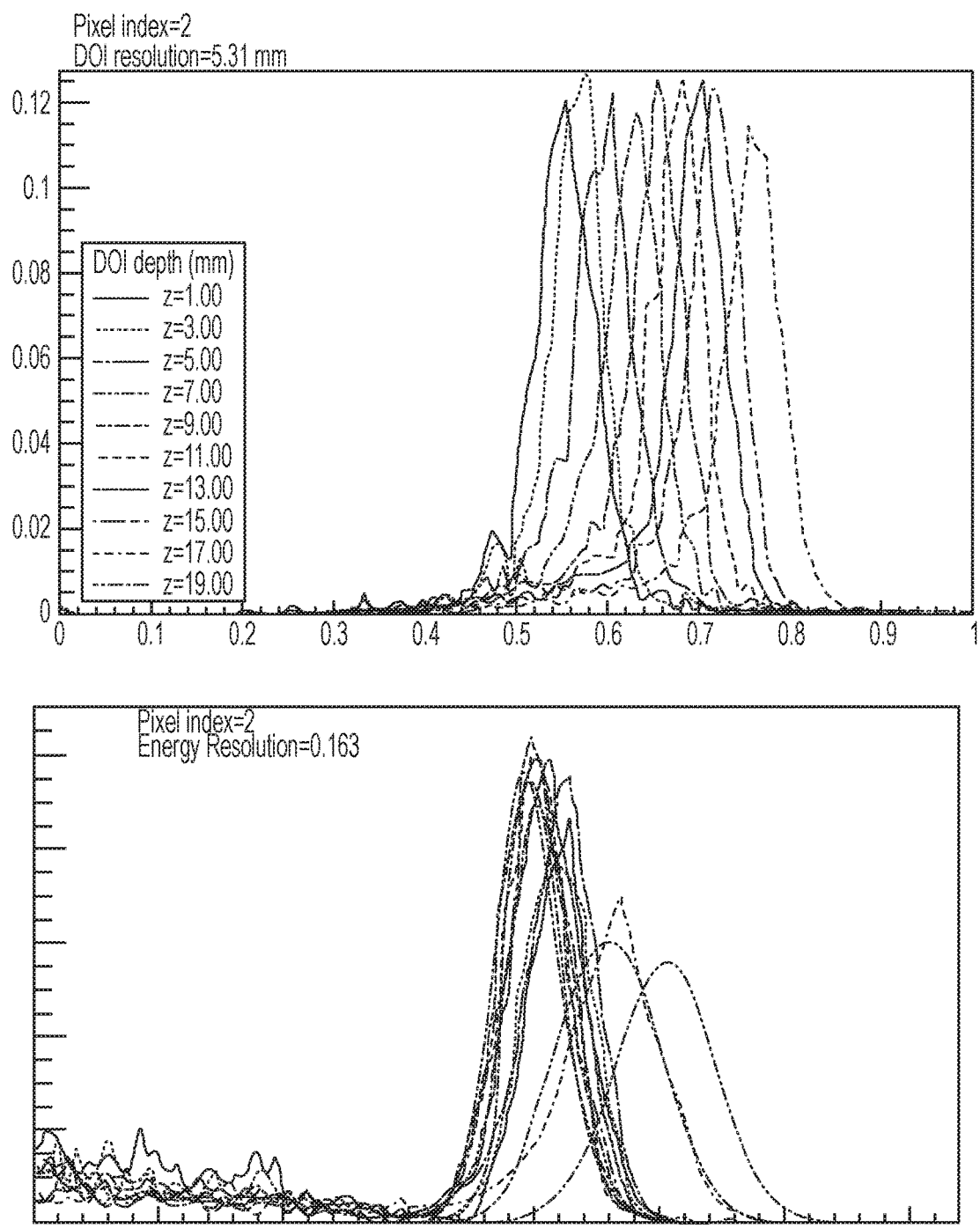
Figure 3C:
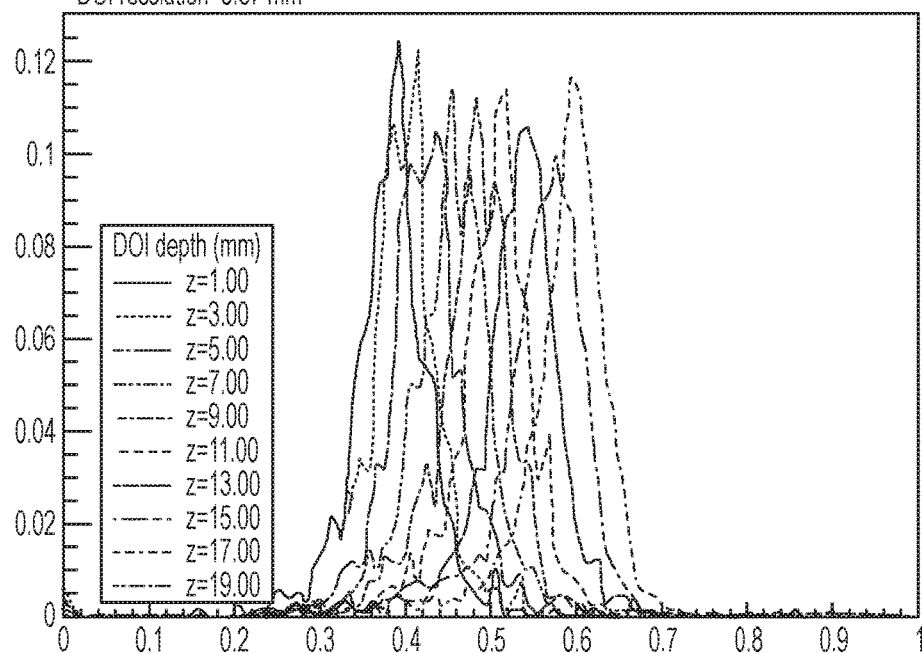
Figure 3C:
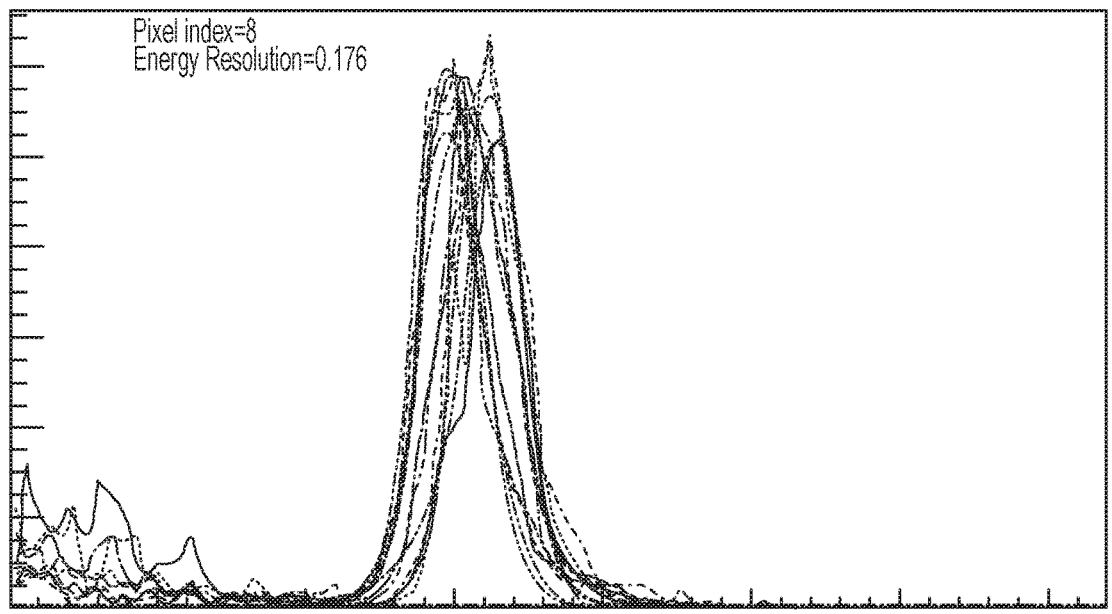

The following section includes Monte Carlo Simulation (GATE) of a 15×15 lutetium orthosilicate (LSO) scintillation-crystal array (2.4 mm pixel) and 8×8 bismuth germanium oxide (BGO) (2.4 mm pixel) array. FIGS. 3A-3C show the DOI point spread function (PSF) and energy spectra of three selected BGO pixel locations. In particular, the figures show the DOI PSF (top) and the energy spectra (bottom) from block corner (FIG. 3A), edge (FIG. 3B), and center (FIG. 3C) of a BGO HR-DOS DOI block.

The performance of both LSO/BGO HR-DOS blocks are summarized in the Table-1. The DOI resolution of the DOS blocks is similar to those of the DOI blocks fully covered by SiPM arrays that were published by others. The XY decoding maps with different decoding methods are shown in FIGS. 4 and 5.

TABLE 1

Performance of two HR-DOS DOI detector blocks

| 2.4 × 2.4 × 20 mm³ pixel | Mean XY Decoding Blurring | Mean Energy Resolution | Mean DOI Resolution |
| --- | --- | --- | --- |
| BGO 8 × 8 | 0.4 mm | 20.2% | 5.47 mm |
| LSO 15 × 15 | 0.8 mm | 24.5% | 4.83 mm |

Figure 4A:
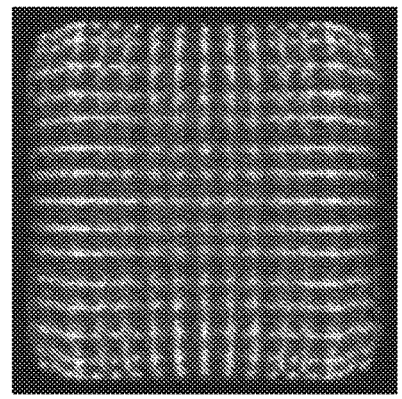
FIGS. 4A-4E display decoding maps of block displays according to exemplary embodiments of the present disclosure.
Figure 4B:
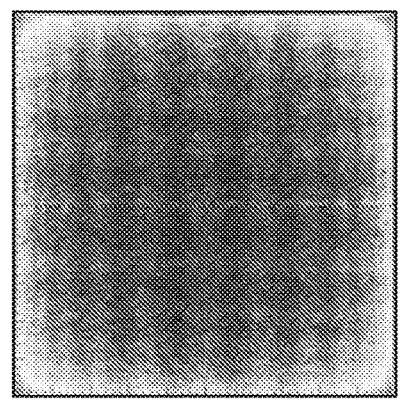
Figure 4C:
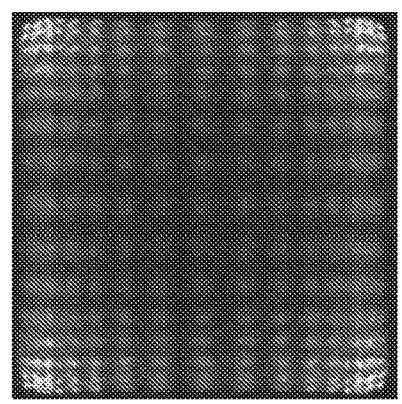
Figure 4D:
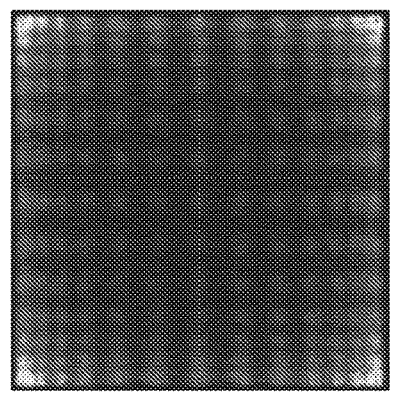
Figure 4E:
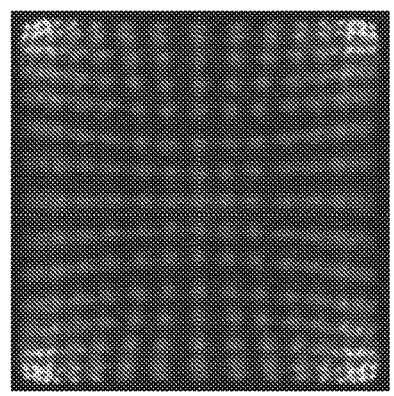
Figure 5A:
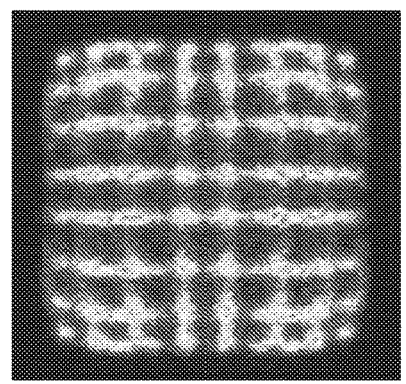
FIGS. 5A-5D display decoding maps of block displays according to exemplary embodiments of the present disclosure.
Figure 5B:
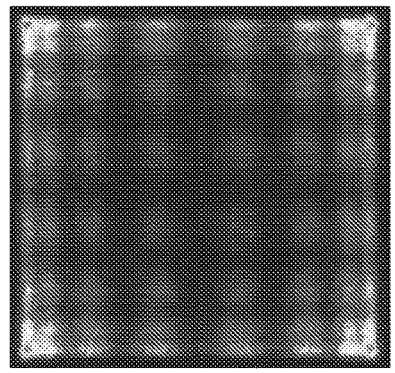
Figure 5C:
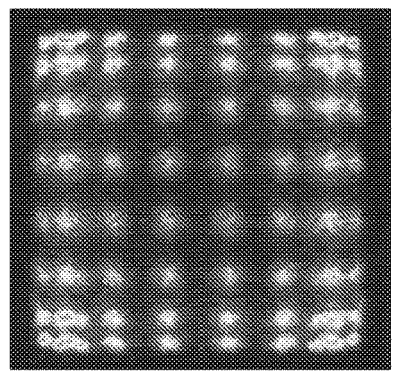
Figure 5D:
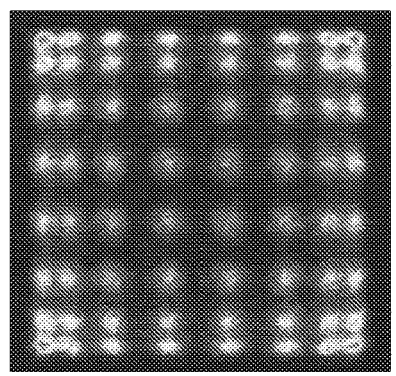

FIGS. 4A-4E show decoding maps of 15×15 LSO block configured similar to that shown in FIG. 2 with different decoding. FIG. 4A shows light-channel decoding, FIG. 4B shows Anger logic decoding (log scale), FIG. 4C shows composite decoding with arithmetic mean, FIG. 4D shows composite decoding with geometric mean, and FIG. 4E shows composite decoding with a complex function.

FIGS. 5A-5D show 8×8 BGO HR-DOS block with (a) Light-Channel decoding, (b) Anger Logic decoding, (c) Composite decoding using arithmetic mean, (d) Composite decoding using geometric mean.

In summary, Monte Carlo simulations shows that a 15×15 LSO detector array (2.4×2.4 mm pixels) can be decoded by 18 SiPMs (2 rows of nine 3×3 mm SiPM) on the top and 18 SiPM at the bottom, thus achieving a 10× reduction in SiPM usage, supporting electronic channels and heat loading (an important engineering issue as the SiPM operation stability is quite heat sensitive). A BGO detector 8×8 array (2.4×2.4 mm pixels) can be achieved with a 6.4× reduction in SiPM. Even comparing to the non-DOI detectors in current clinical systems, there is a 5× (3×) SiPM reduction for LSO (BGO) respectively. The 2.4×2.4 mm detector pixel size (image resolution) that can be achieved with the new DOS (HR-DOS) design is also superior to the current detector resolution of 3.5-4 mm in current clinical PET, PET/CT and PET/MR systems. The DOI data from the DOS design can improve the severe resolution-blurring for points away from the center of the field of view. In addition to higher resolution (both at center and at large radius), the design can potentially allow PET to be designed to increase PET detection senstivity of 10-20 times by enabling the axial field of view of PET to be increased by 4-5 times from current systems Additional embodiments include low-cost high-resolution depth-of-interaction (DOI) PET-detector designs, which may be practical (economical) enough to be implemented into clinical PET/CT and PET/MR systems. These designs use even less light sensors (e.g SiPMs) and supporting electronics than do the current non-DOI PET detectors used in current clinical systems, thus clinical PET/MR and PET/CT with DOI information may become a reality while reducing the production cost of such systems. The lower-cost DOI-PET detectors may be used to improve PET resolution and to significantly improve image quality by (a) enabling the development of ultra-long axial field-of-view clinical PET, (b) increasing the thickness of scintillation crystals, and (c) reducing the diameter of the PET detector ring. The lower-cost DOI PET detectors can also be used for compact brain PET, breast PET and clinical PET/MR systems that require the PET detector-ring size to be reduced significantly to fit into the bore of the MR system.

A robust and simple direct way to measure DOI (Z) is to have two 2D light sensor or detector arrays coupled to the top and the bottom ends of a scintillator array respectively. For an N×N scintillation-crystal array, the dual-end read-out requires $2N^2$, thus doubling the cost of costly read-out sensors (e.g. SiPMs), associated read-out electronics, and heat generation, comparing to a non-DOI detector array. The dual-ended read-out approach can be adopted in principle for its robust and direct way of determining the DOI position (Z). In addition, one can decipher the X and Y positions of the scintillating crystals in the array using much fewer detector channels.

Disclosed embodiments include: (a) a Dichotomous Sparse Quadrant-Sharing (DSQS) DOI design that reduces the number of SiPM usage to $N^2/2$, thus using half the number of detectors (e.g. SiPMs) of the conventional non-DOI detector design, and (b) a Dichotomous Orthogonal Symmetry (DOS) DOI design that reduces the number of detectors (e.g. SiPMs) used to 4N, compared to the $N^2$ of SiPM used in the conventional non-DOI detectors.

Dichotomous Offset Quadrant Sharing (DO-QS) DOI Detector Design

Figure 6:
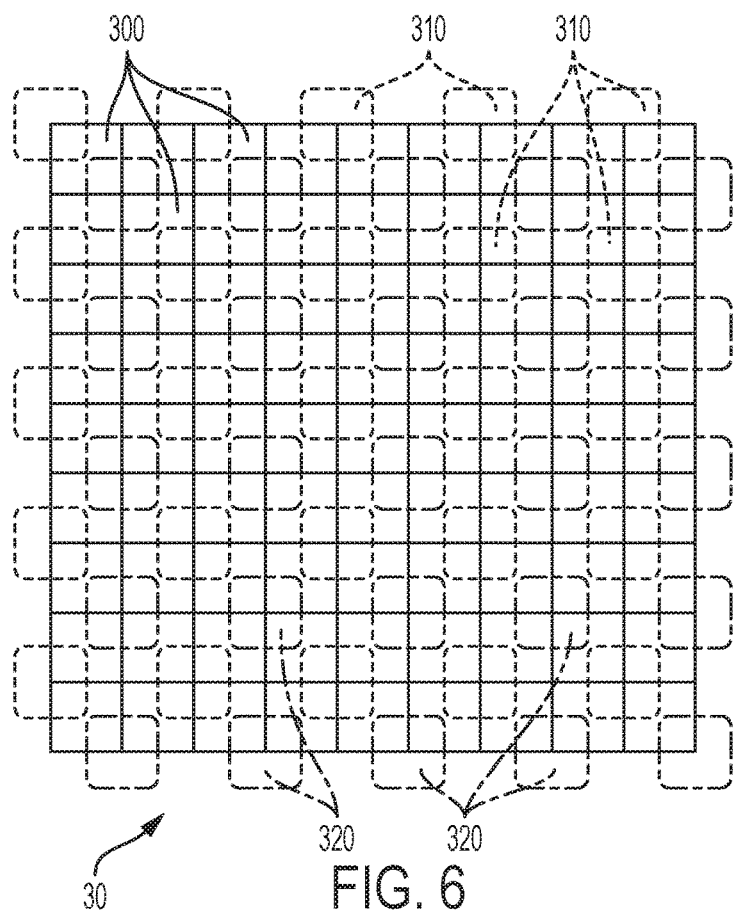
FIG. 6 displays a top view of an apparatus according to exemplary embodiments of the present disclosure.
Figure 7:
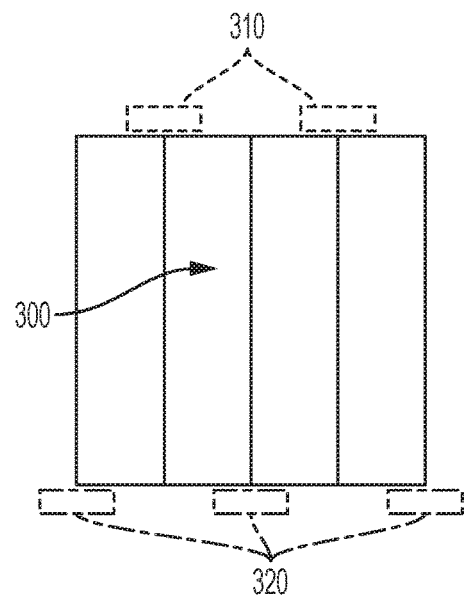
FIG. 7 displays a side view of the embodiment of FIG. 6.

Referring now to FIGS. 6 and 7, in another embodiment an apparatus 30 includes an N×N (e.g. 9×9 in the embodiment shown) scintillator array 300 constructed with individual scintillator pixels, each of which is fully covered with reflective material. FIGS. 6 and 7 show the dichotomous offset quadrant sharing (DO-QS) depth-of-interaction detector design with four crystals coupling to one sensor at each end. FIG. 6 shows a top view and FIG. 7 shows a partial side view.

In this embodiment, the scintillation photons are confined inside each pixel and light is directed to exit the detector pixel from the two opposing narrow ends. Assuming the light sensors (e.g. SiPMs in certain embodiments) and the crystal pixels are the same size, a first planar array 310 $(1+N/2)\times(1+N/2)$ of light sensors is mounted at the top end of an array of crystals 300 (e.g. scintillation pixels), alternatingly skipping over every other crystal 300. Array 310 is shown in red in FIGS. 6-7. A second array 320 of light sensors is mounted onto the bottom end of scintillator array 300 with the center of the sensors offset diagonally from the center of the sensors in array 310 by one scintillation crystal 300. Array 320 is shown in blue in FIGS. 6-7. Hence, each sensor is optically coupled to four scintillator pixels or crystals (e.g. quadrant-sharing), equally collecting photons from the four pixels. The distance between each sensor in arrays 310 and 320 is twice the pitch size of scintillator array 300. In this setup, each scintillator pixel in array 300 is symmetrically coupled to two sensors at both ends; therefore, the DOI position (Z) can be measured by the signal difference between the top and bottom sensor in arrays 310 and 320. The firing scintillator pixel positions (X and Y) are uniquely determined by matching the simultaneous signal arrival of a top sensor ($T_{ij}$) to one of its four "neighboring" bottom sensors, namely, sensor $B_{i-1,\ j-1}$), sensor ($B_{i-1,\ j-1}$), sensor ($B_{i-1,\ j+1}$), sensor ($B_{i+1,\ j+1}$). Alternatively, the X-Y positions can be determined by matching the simultaneous signal arrival of each bottom sensor with one of its four "neighboring" top sensors. In certain embodiments, the gaps between sensors in arrays 310 and 320 visible in the end view of FIG. 6 can be covered by a light-modulating material, including for example, a light-absorbing material or a light-reflecting material.

The embodiment shown in FIGS. 6-7 provides many advantages. For example, lower costs are possible in view of the sensor configuration and associated electronics. In particular embodiments, the scintillator array is decoded by two sparse SiPM arrays. The SiPM to scintillator pixel ratio is much smaller than conventional block detector design that requires a full coverage of the entire scintillator module. For example, in the schematic figure, there are N by $N=N^2$ scintillators, the proposed depth-of-interaction (DOI) detector would use $2((N+1)/2)^2$ or $(N+1)^2/2$ SiPM whereas a regular DOI detector design would use $2N^2$ SiPM's, thus resulting in a $4N^2/(N+1)^2$ times reduction in SiPM usage. When N is large, there is nearly a 4 times reduction in the usage of supporting electronics (amplifiers, ADC, buffers and logical gates). When N is a small number, the cost-reduction of the proposed design is slightly less because of the extra edge sensors. For example, for a small module or array with N=9, there are 81 scintillators and 50 SiPM's, or a 3.24 times cost reduction (compare with a regular dual-end read-out DOI detector). For N=25, there are 625 scintillator pixels and 169 SiPM's, which is a 3.7 times in cost reduction. Even comparing to a conventional detector array without DOI capability, there is still nearly a 2 times reduction in SiPM and read-out electronic cost.

In addition, analog-decoding is not necessary in the embodiment shown in FIGS. 6-7. Hence, there is not complex light guide or light-sharing masks between individual scintillator pixels to create an analog-decoding scheme. Therefore, one can construct a large-area detector module with a simplified manufacturing process and the construction cost of the PET detector system can be reduced. Furthermore, since there is no analog decoding, it is a mathematically robust and there is no analog-decoding degradation in resolution (the so-called "block-decoding" effect). Accordingly the imaging spatial resolution can be better than an analog-decoding block-detector design.

With the proposed DOI detector design shown in FIGS. 6-7, the timing measurement of the arrival of a detected gamma ray can be more accurately determined because the interaction depth measured (DOI) can be used to correct for the flight time of the gamma ray within the long (deep) scintillator pixel in real time for each event. Thus for time-of-flight (TOF) PET systems, the TOF time resolution may be improved with this configuration to provide a higher image quality (e.g. images with less noise).

Accordingly, the configuration shown in FIGS. 6-7 can achieve a low-cost large-area PET detector module with DOI capability with only 25 percent of the costly sensors (e.g. SiPMs) and electronics comparing to the conventional dual-end DOI PET design. When compared to the conventional non-DOI detector used in current clinical PET, the costly SiPM read-out cost can be reduced by nearly 50 percent, while providing a higher imaging resolution and better time-of-flight resolution for better image quality. The heat load of electronics can be reduced proportionally.

In particular embodiments using the popular 3×3 mm$^2$ SiPM implemented, 3×3 mm$^2$ scintillation-crystal pixels can be used. Since there is one crystal gap between two neighboring SiPM on the same plane, this gap can accommodate the packaging material at the perimeter of a SiPM (typically 0.5-1 mm). As there is no analog-decoding, such as the Anger analog decoding, to decode the firing crystal, the typical block-decoding blurring effect will not exist to degrade the imaging resolution.

Dichotomous Offset Quadrant-Sharing (DO-QS) DOI Ultrahigh Resolution Designs

Figure 8:
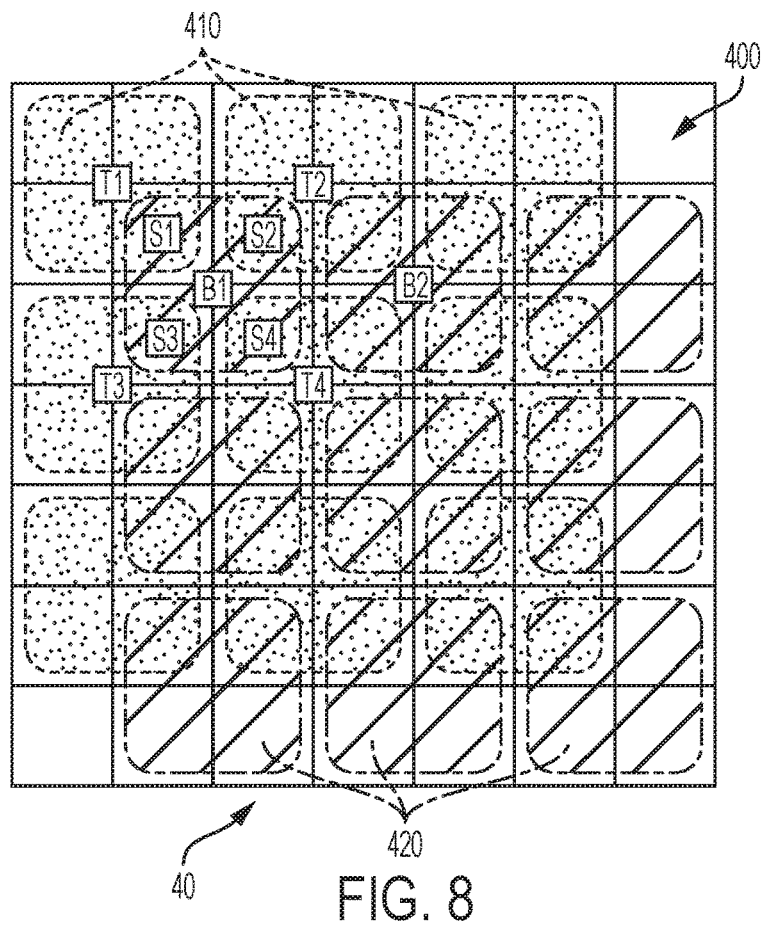
FIG. 8 displays a top view of an apparatus according to exemplary embodiments of the present disclosure.
Figure 9:
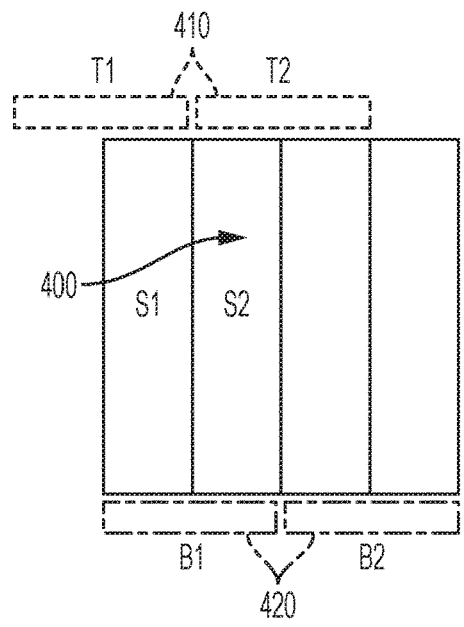
FIG. 9 displays a side view of the embodiment of FIG. 8.

Referring now to FIGS. 8-9, a DO-QS DOI detector design can also be implemented to improve resolution (reducing crystal-pixel size). FIG. 8 shows a top view and FIG. 9 shows a partial side view. Similar to the previously-described embodiment, this embodiment comprises an apparatus 40 including an array of crystals 400 with sensors 410 and 420 coupled to opposite ends of the crystals. However, if the crystal pixel size in FIG. 6 is shrunk in both X-Y dimensions while the size of sensors 410 and 420 is kept constant, the gaps between two neighboring sensors are reduced until the crystal size is reduced by half in both X-Y dimensions. Note that the center of the sensors 410 and the center of the sensors 420 are kept offset diagonally by one crystal, when the size of crystal shrank. The X-Y decoding principle of DO-QS described above regarding FIGS. 6-7 can also be used in this embodiment. The DO-QS design is altered to that shown in FIGS. 8-9, whereby all the gaps between neighboring sensors are eliminated.

When scintillation-crystal S1 detects an event, only the top sensor T1 and the bottom sensor B1 will receive signal, thus determining the X-Y position of S1, while the difference in signal of T1 and B1 determines the depth of interaction (e.g. the Z-dimension). Similarly, the firing of S2 is determined by the coincidental signal detection of T2 and B1.

In a particular embodiment using sensors configured as 3.5×3.5 mm$^2$ SiPM (including a packaging edge of 0.5 mm), an ultrahigh-resolution (small) crystal pixel size of 1.75× 1.75 mm$^2$ can be achieved.

Figure 10:
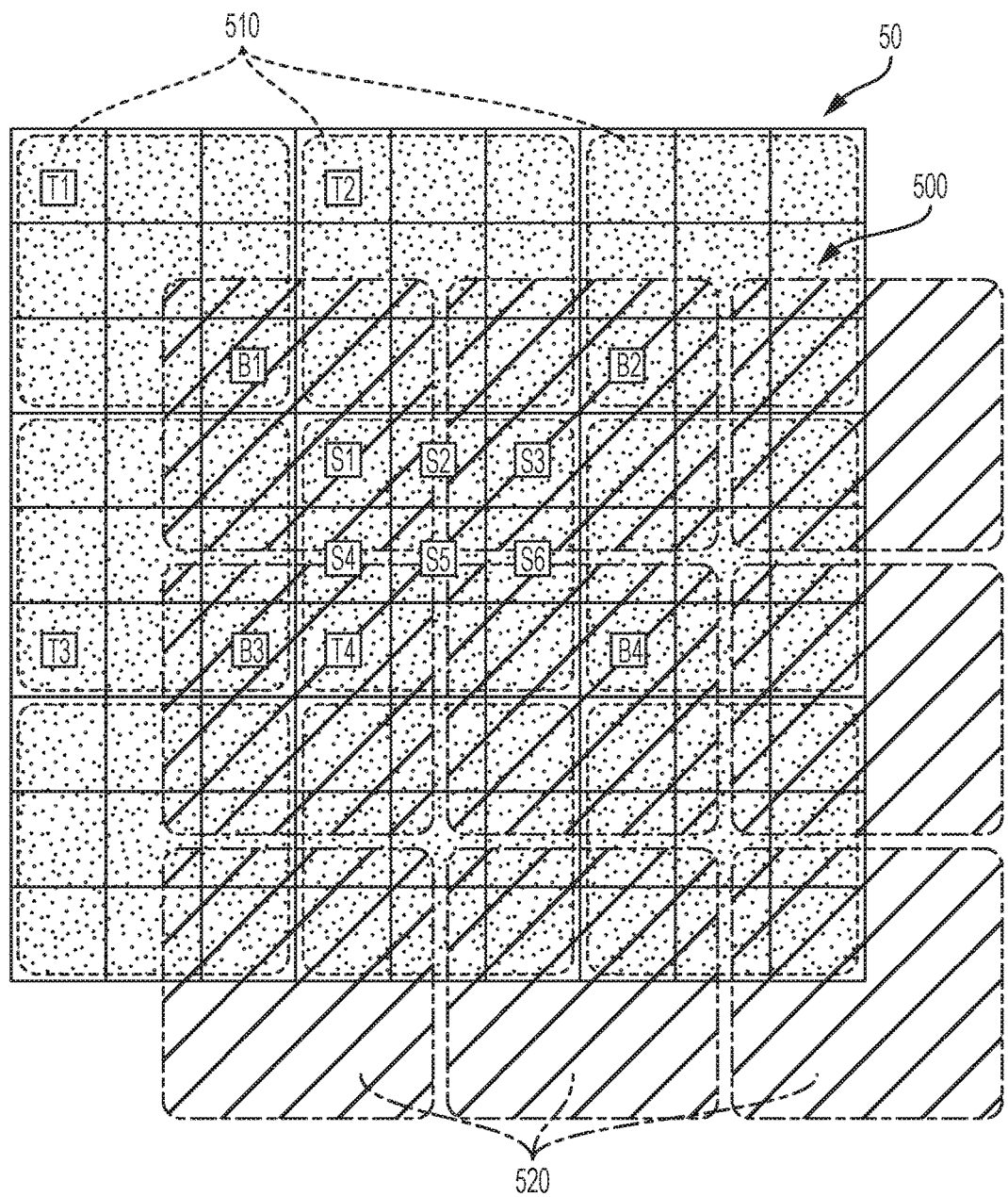
FIG. 10 displays a top view of an apparatus according to exemplary embodiments of the present disclosure.
Figure 11:
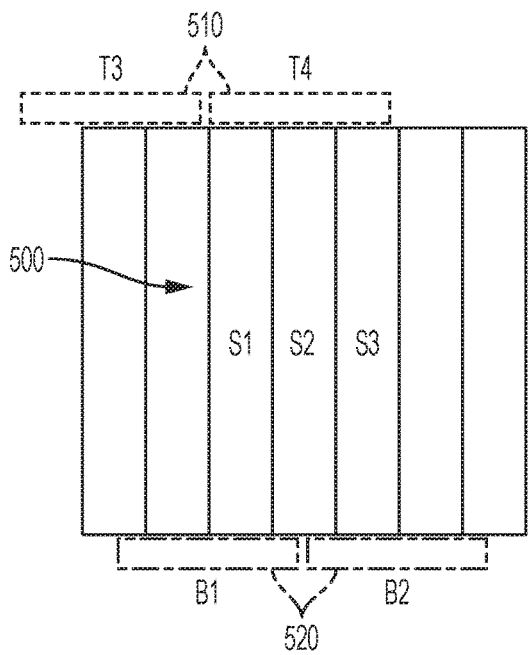
FIG. 11 displays a side view of the embodiment of FIG. 10.

In specific embodiments, the DO-QS DOI detector design can be extended further to have one SiPM coupling to 9 crystals (a 3×3 array), without resorting to the Anger-analog decoding for decoding the firing crystal pixel. Referring now to FIGS. 10-11, one such embodiment comprises an apparatus 50 including sensors 510 (shown in red) and 520 (shown in blue) coupled to opposite ends of an array of crystals 500. The center of the sensors 510 and the center of the sensors 520 are offset diagonally by 1.5 crystal in this embodiment.

In the embodiment shown, when crystal S1 of crystal array 500 emits light, it will trigger sensor T4 of array 510 and sensor B1 of array 520. When crystal S2 of crystal array 500 emits light, it will trigger sensors T4 of array 510, and sensors B1 and B2 of array 520. When crystal S3 of crystal array 500 emits light, it will trigger sensor T4 of array 510 and sensor B2 of array 520. When S4 of crystal array 500 emits light, it will trigger sensor T4 of array 510, and sensors B1 and B3 of array 520. When S5 of crystal array 500 emits light, it will trigger sensor T4 of array 510, and sensors B1, B2, B3 and B4 of array 520.

In specific embodiments using the 3.5×3.5mm$^2$ SiPM (including a packaging edge of 0.5 mm), an ultrahigh-resolution crystal-pixel size of 1.16×1.16 mm$^2$ can be achieved.

Experimental Results

Figure 12A:
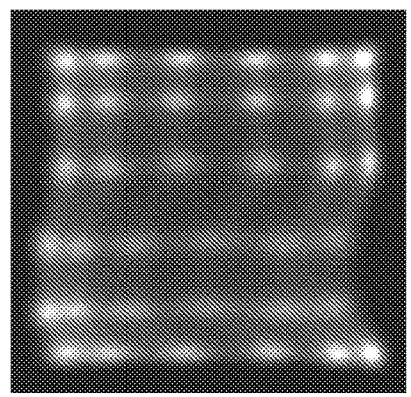
FIGS. 12A-12C display decoding maps of block displays according to exemplary embodiments of the present disclosure.
Figure 12B:
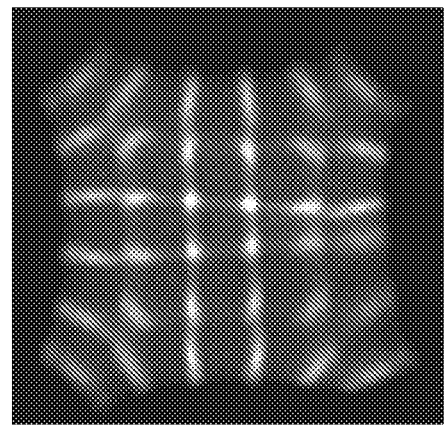
Figure 12C:
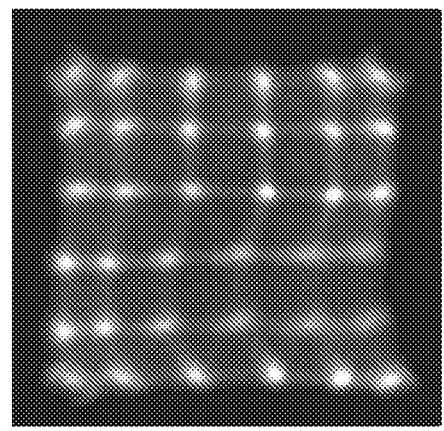

A 6×6 array of LYSO crystals (each 4×4×20 mm$^3$) was developed. Twenty four SiPM (SensL MicroFB-30035) were coupled to the crystal array as shown in FIG. 1 to create a detector block with the DOS DOI design. The array was first exposed to a radiation flood source (Cs-137). The inventors acquired the 2-D decoding (X-Y) data which combined the interactions at all depths, as in a regular non-DOI block. The results are shown in FIGS. 12A-12C. FIG. 12A shows Anger decoding, FIG. 12B shows light-channel decoding and FIG. 12C shows geometrical mean decoding.

As shown in FIGS. 12A-12C, the Anger method has the widest point spread functions but less dependent on the depth of interaction. Secondly, with the light-channel decoding, each crystal has a line or comet shape, except for the four central crystals; the comet shape may be the effect of the interaction depth. The inventors hypothesize that the each part of the comet shape corresponded to a different interaction depth. Hence, the light-channel crystal-pixel decoding map may be interaction-depth dependent. Thirdly, the geometrical mean of the Anger decoding and the light-channel decoding yielded the best 2-D pixel decoding with tighter (narrower) point spread functions. The geometrical mean is only one way to weight the contribution from both the Anger decoding and the light-channel decoding; the DOS design allows a variety of different weighted-mean methods. A smart weighted mean, as a function of X-Y positions and/or interaction-depth positions, may improve the 2-D pixel-decoding resolution.

Figure 13:
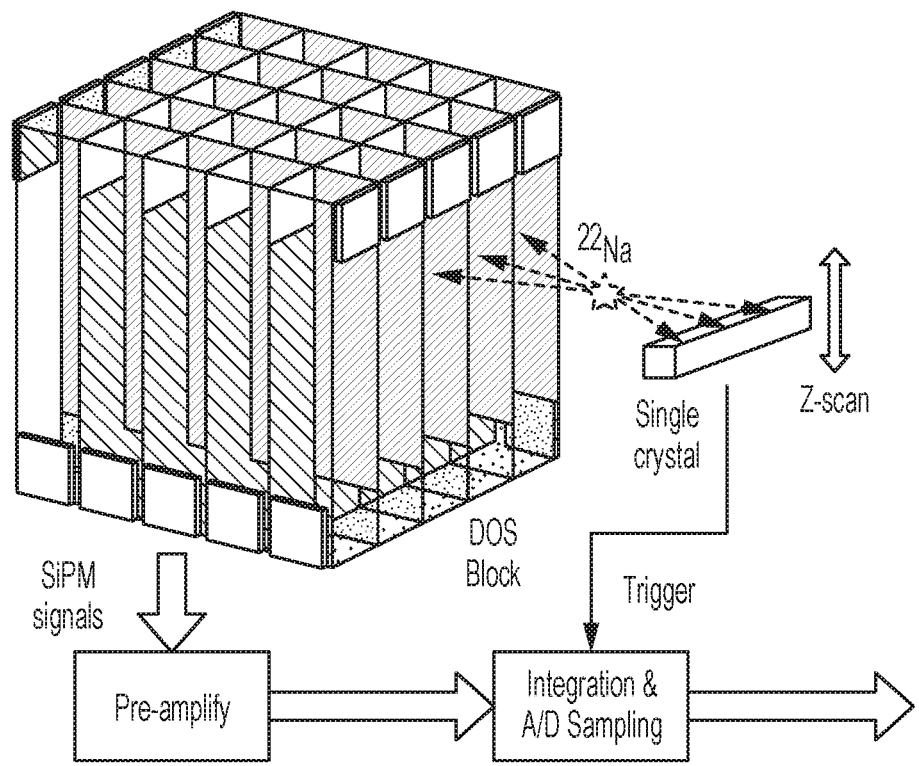
FIG. 13 shows a schematic of an experimental setup to obtain data shown in FIG. 14A-14F.
Figure 14A:
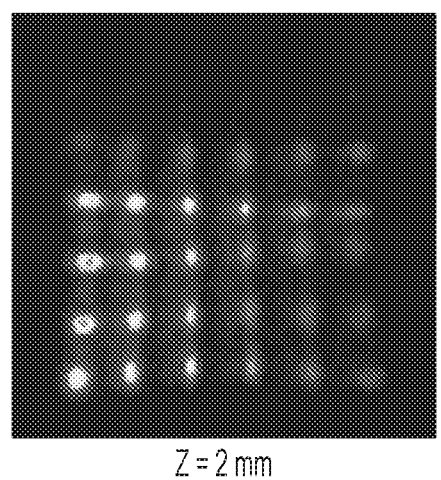
FIGS. 14A-14F shows display decoding maps of block displays according to exemplary embodiments of the present disclosure.
Figure 14B:
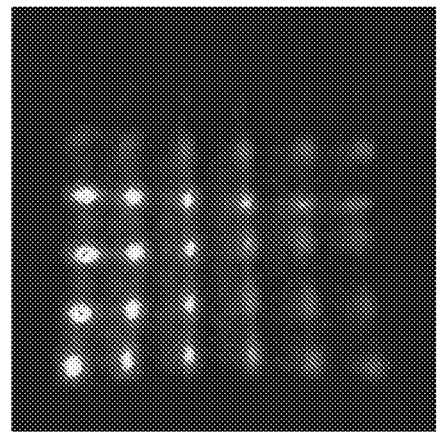
Figure 14C:
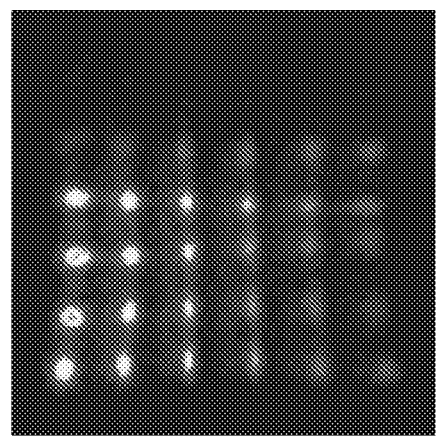
Figure 14D:
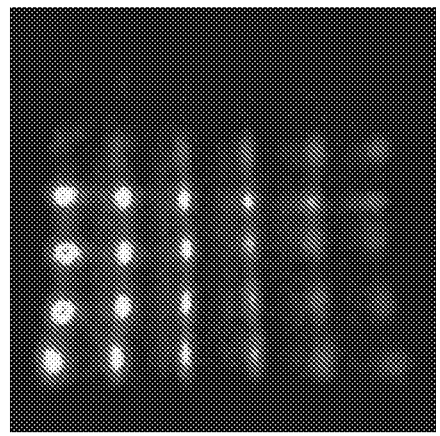
Figure 14E:
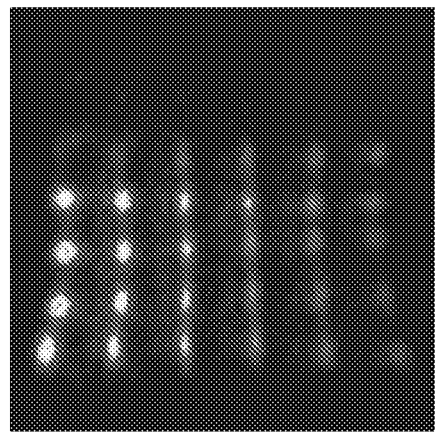
Figure 14F:
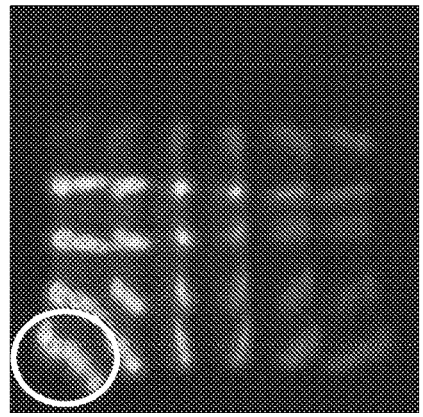
Figure 15A:
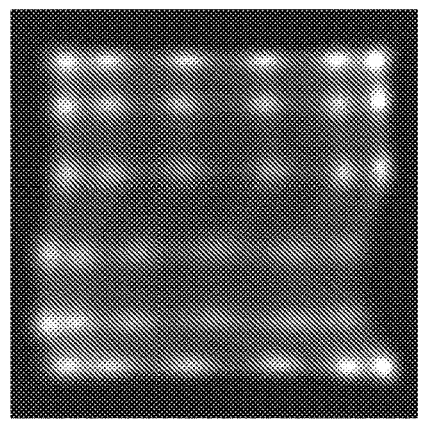
FIGS. 15A-15D shows display decoding maps of block displays according to exemplary embodiments of the present disclosure.
Figure 15B:
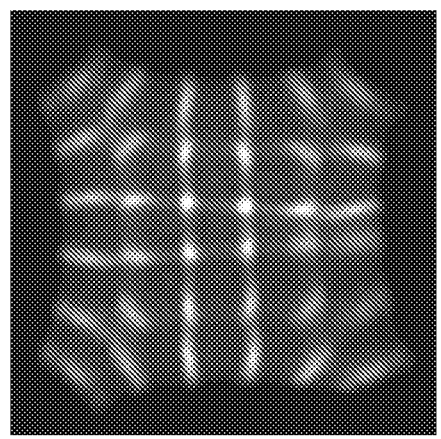
Figure 15C:
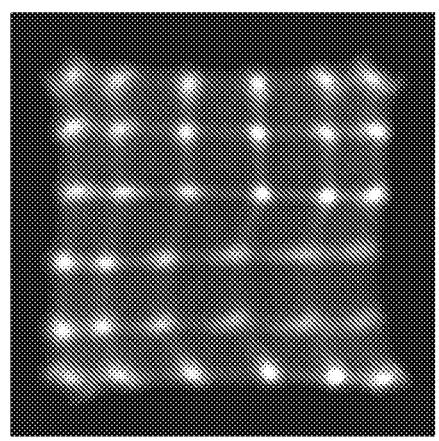
Figure 15D:
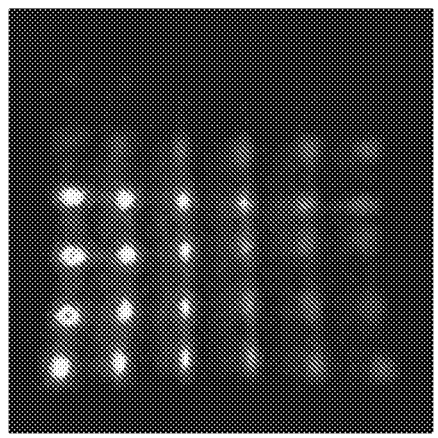

To test this hypothesis, the inventors investigated the 2-D crystal-pixel decoding as a function of interaction depths (Z). This is especially germane for the light-channel decoding method because the inventors hypothesized that the comet shapes (FIG. 12B) of the decoded crystals were the effect of DOI. If the DOI is first calculated by the difference in the signal amplitudes between the top and bottom SiPM's, the DOI information can be input into the weighted-mean function to create a better 2-D pixel-decoding map to achieve higher spatial resolution. To test this hypothesis experimentally, the inventors set up the DOS detector block as shown in FIG. 13. A single crystal (2.4×2.4×15 mm$^3$) was placed orthogonal to the crystal length in the block.

A positron point source (Na-22) was placed between the crystal block and the single crystal. The distance from the single crystal to the source was 3 cm and the distance from the source to the block was also 3 cm. Coincidence events between the block and the single crystal were collected. With this setup, the coincidence events detected were on a thin slice of the interaction depth constrained by the co-linearity of the narrow 2.4-mm crystal and the positron point source. The slice thickness ($\Delta Z$) of the interaction depth (Z) is about 2.4 mm as defined by the width of the single crystal. The source and single crystal were moved synchronously (Z-scan) to five different depths (Z=2, 4, 6, 8, 10 mm) to select the events interacted at each of these depths inside the crystal block.

The 2-D crystal-pixel decoding maps measured at each interaction depth, using only the light-channel decoding method, are shown in FIG. 14.

The narrow "point spread function" of each crystal decoded in FIG. 14 shows that if the measured interaction depth is used for gating the 2-D crystal-pixel decoding, the crystal decoding will be improved (less blurring). The 2-D crystal-pixel decoding using different decoding algorithms enabled by the DOS DOI detector block are shown in FIG. 15.

FIG. 15 shows that among the four decoding algorithms shown, the traditional Anger decoding has the worst decoding resolution while the depth-gated light-channel decoding has the best resolution. From FIG. 14 and FIG. 15, the depth-gated light-channel decoding maps showed very large decoding gaps between each of the 4-mm crystal pixels; such a large decoding gap between crystal pixels can easily accommodate an additional crystal pixel between the original crystal pixels. In other words, the high decoding resolution would allow the original crystal pixel size of 4×4 mm (6×6 array) to be reduced by half to 2×2 mm$^2$ (12×12 array) with the proposed DOS 3-D decoding detector design. Hence the proposed DOS 3-D decoding DOI detector design can be used to build ultrahigh-resolution PET systems, which is especially beneficial for the brain and small animal PET applications.

The decoding methods, shown in FIG. 15, are not all the decoding schemes possible with the proposed DOS DOI detector design. For example, we can (a) combine the geometrical-mean method and the depth-gated method, or (b) weighting the geometrical mean method by an X-Y weighting function such as giving the best X-Y region of the light-channel data a larger weight than the corresponding Anger data, or (c) combining the depth-gating, the geometric mean and an optimal X-Y weighting function, etc. We will investigate these combined schemes in the future to derive the best 2-D crystal-pixel decoding, which would lead to the improvement in imaging spatial resolution of a PET system.

CONCLUSION

The incorporation of depth-of-interaction measurements in PET systems has become more important, because of (a) the recent improvement (reduction) in the scintillation-crystal pixel size in clinical systems, (b) the clinical need of increasing the axial field-of-view of PET, and (c) the radiation-dose concern, and the clinical need of shorter scan time (more patient throughput). Although the depth-of-interaction (DOI) PET detector concept was proposed more than 3 decades ago [27] for improving spatial resolution, detection sensitivity and spatial data sampling, DOI has yet to be incorporated into the current clinical PET/CT/MR systems. The Achilles tendon of DOI detectors preventing its deployment in clinical PET systems is the high production cost due to the substantial increase in the photo-sensors and the signal-processing electronics.

A "Dichotomous-3D" DOI PET detector design approach is proposed here. This approach can potentially reduce the production cost of incorporating DOI in PET systems because the photo-sensors usage and electronic complexity are even less than that of the current non-DOI PET detectors. The "Dichotomous-3D" approach can be implemented in 2 ways:

(a) The Dichotomous-Offset-Quadrant-Sharing design (DO-QS) which is deterministic and has good timing resolution for time-of-flight PET (from Monte Carlo simulation TOF<400 ps).

(b) The Dichotomous-Orthogonal-Symmetric light-channel DOI design which would reduce SiPM/electronics usage even more, but the time resolution may be degraded for TOF; however, it can be deployed for building low-cost high-sensitivity BGO PET systems with long axial-field-of-views.

Both of these lower-cost DOI designs are suitable for developing very long axial-field-of-view PET (1-2 meters) for imaging the entire torso at the same time to significantly improve detection sensitivity and perform whole-body dynamic imaging to extract quantitative physiological parameters of the whole body at the same time. Both can reduce the production cost of DOI PET to below that of non-DOI PET.

The DO-QS detector design can also definitely decode nine 1×1 mm$^2$ crystal pixels using the much larger 3×3 mm$^2$ SiPM for building ultrahigh-resolution brain PET and animal PET with nine crystals coupling to one SiPM, thereby reducing the SiPM and supporting electronics by 9 times.

The proposed DOS DOI detector design may also improve the 2-D crystal-pixel decoding resolution over the traditional Anger decoding by a combination of depth-gating and/or XYZ position-weighted mean algorithms. Hence, the DOS DOI detector design can be used for building ultrahigh-resolution PET systems.

* * *

All of the devices, apparatus, systems and/or methods disclosed and claimed herein can be made and executed without undue experimentation in light of the present disclosure. While the devices, apparatus, systems and methods of this invention have been described in terms of particular embodiments, it will be apparent to those of skill in the art that variations may be applied to the devices, apparatus, systems and/or methods in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

The contents of the following references are incorporated by reference herein:

1. U.S. Pat. 7,238,946
2. U.S. Pat. 7,291,841
3. U.S. Pat. 7,626,389
4. U.S. Pat. 7,671,339
5. U.S. Pat. 8,115,174
6. U.S. Pat. 8,384,040
7. U.S. Pat. 8,405,038
8. U.S. Pat. 8,809,790
9. U.S. Pat. 8,946,643
10. U.S. Pat. 8,963,093
12. U.S. Pat. Publ. 2005/0253073
13. U.S. Pat. Publ. 2007/0096031
14. U.S. Pat. Publ. 2011/0192982
15. U.S. Pat. Publ. 2012/0307025
16. U.S. Pat. Publ. 2013/0028379
17. U.S. Pat. Publ. 2013/0009067
18. U.S. Pat. Publ. 2013/0153774
19. U.S. Pat. Publ. 2014/0264041
20. U.S. Pat. Publ. 2014/0110592
21. PCT Pat. Publ. WO2013166574
22. PCT Pat. Publ. WO2014181232
23. Orita et al., Three-Dimensional Array of Scintillation Crystals with Proper Reflector Arrangement for a Depth of Interaction Detector, IEEE Trans. Nucl. Sci., vol. 52, no. 1, pp. 8-14.
24. Ito et al., Positron Emission Tomography (PET) Detectors with Depth-of-Interaction (DOI) Capability, Biomed Eng. Lett. (2011) 1:70-81.
25. Moehrs, et al., A detector head design for small-animal PET with silicon photomultipliers (SiPM) Phys. Med. Biol. 51 (2006) 1113-1127.
26. Kwon, et al., Development of Small-Animal PET Prototype Using Silicon Photomultiplier (SiPM): Initial Results of Phantom and Animal Imaging Studies, J. Nucl. Med. 2011; 52:572-579.
27. Taghibakhsh, et al., Silicon photomultipliers for positron emission tomography detectors with depth of interaction encoding capability, A633 (2011) S250-S254.
28. Wong W-H: Designing a stratified detection system for PET cameras. IEEE Transactions on Nuclear Science 33(1):591-596, 1984.
29. Zhang, et al., Lower-cost Depth-of-Interaction PET Detector Designs Using Dichotomous-3D Decoding, 2015 IEEE Nuclear Science Symposium and Medical Imaging Conference Record.

The invention claimed is:

1. An apparatus for optical emission detection, the apparatus comprising:
a block comprising scintillation crystals configured in an arrangement having X-Y-Z dimensions;
a first linear one-dimensional array of light sensors coupled to a column of scintillation crystals parallel to the X-dimension;
a second linear one-dimensional array of light sensors coupled to a row of scintillation crystals parallel to the Y-dimension, wherein the second linear one-dimensional array of light sensors is spaced apart from the first linear one-dimensional array of light sensors in the Z-dimension; and
reflecting film coupled to a plurality of scintillation crystals of the block, wherein:
a first portion of the reflecting film is coupled to one or more sides of a first plurality scintillation crystals, wherein the first portion of the reflecting film is parallel to the first linear one-dimensional array of light sensors;
a second portion of the reflecting film is coupled to one or more sides of a second plurality scintillation crystals, wherein the second portion of the reflecting film is parallel to the second linear one-dimensional array of light sensors;
the first portion of the reflecting film is offset from the second portion of the reflecting film in the Z-dimension; and
the apparatus does not comprise light sensors in the Z-dimension between the first linear one-dimensional array of light sensors and the second linear one-dimensional array of light sensors.

2. The apparatus of claim 1 wherein:
the first linear one-dimensional array of light sensors is coupled to a first end of the block;
the second linear one-dimensional array of light sensors is coupled to a second end of the block;
the first portion of the reflecting film is not coupled to the first end of the block; and
the second portion of the reflecting film is not coupled to the second end of the block.

3. The apparatus of claim 2 wherein:
the first portion of the reflecting film is not coupled to any scintillation crystals on a plane of scintillation crystals comprising the column of scintillation crystals to which the first linear one-dimensional array of light sensors is coupled; and
the second portion of the reflecting film is not coupled to any scintillation crystals on a plane of scintillation crystals comprising the row of scintillation crystals to which the second linear one-dimensional array of light sensors is coupled.

4. The apparatus of claim 3 further comprising:
a third linear one-dimensional array of light sensors coupled to a second column of scintillation crystals of the scintillation crystal block, wherein the third linear one-dimensional array of light sensors is parallel to the first linear one-dimensional array of light sensors;
a fourth linear one-dimensional array of light sensors coupled a second row of scintillation crystals of the scintillation crystal block, wherein the fourth linear one-dimensional array of light sensors is parallel to the second linear one-dimensional array of light sensors;
the apparatus does not comprise light sensors in the Y-dimension between the first linear one-dimensional array of light sensors and the third linear one-dimensional array of light sensors; and
the apparatus does not comprise light sensors in the X-dimension between the second linear one-dimensional array of light sensors and the fourth linear one-dimensional array of light sensors.

5. The apparatus of claim 1 wherein:
the first portion of the reflecting film comprises a first plurality of openings; and
the second portion of the reflecting film comprises a second plurality of openings.

6. The apparatus of claim 5 wherein:
the first portion of the reflecting film forms a first plurality of channels for light transmission across columns of scintillation crystals at a first end of the block;
the second portion of the reflecting film forms a plurality of channels for light transmission across rows of scintillation crystals at a second end of the block;
the first plurality of openings is configured to allow light to be distributed between the first plurality of channels for light transmission; and the second plurality of openings is configured to allow light to be distributed between the second plurality of channels for light transmission.

7. The apparatus of claim 1 wherein the first and second linear one-dimensional arrays of light sensors comprise silicon photomultipliers.

8. The apparatus of claim 1 wherein:
the block comprises segmented scintillation crystals segmented into several sections and optically glued back.

9. An apparatus configured as positron emission detector, the apparatus comprising:
a block comprising scintillation crystals configured in an arrangement having X-Y-Z dimensions;
reflecting film coupled to the scintillation crystals;
a first linear one-dimensional array of light sensors coupled to a first plurality scintillation crystals;
a second linear one-dimensional array of light sensors coupled to a second plurality of scintillation crystals, wherein the second linear one-dimensional array of light sensors is spaced apart from the first linear one-dimensional array of light sensors in the Z-dimension; and
a processor configured to analyze data from the first and second linear one-dimensional array of light sensors, wherein:
the processor is configured to calculate the X-Y-Z dimensions of a scintillation crystal emitting light detected by both a first light sensor in the first linear array of light sensors and by a second light sensor in the second linear array of light sensors; and
the apparatus does not comprise light sensors in the Z-dimension between the first linear one-dimensional array of light sensors and the second linear one-dimensional array of light sensors.

10. The apparatus of claim 9 wherein the first and second linear one-dimensional arrays of light sensors are orthogonal to each other.

11. The apparatus of claim 9 wherein:
the first linear one-dimensional array of light sensors is coupled to a column of scintillation crystals; and
the first linear one-dimensional array of light sensors is coupled to a row of scintillation crystals.

12. The apparatus of claim 9 wherein:
a first portion of the reflecting film is not coupled to the column of scintillation crystals to which the first linear one-dimensional array of light sensors is coupled;
a second portion of the reflecting film is not coupled to the row of scintillation crystals to which the second linear one-dimensional array of light sensors is coupled.

13. The apparatus of claim 12 wherein:
the first portion of the reflecting film is not coupled to any scintillation crystals on a plane of scintillation crystals comprising the row of scintillation crystals to which the first linear one-dimensional array of light sensors is coupled; and
the second portion of the reflecting film is not coupled to any scintillation crystals on a plane of scintillation crystals comprising the column of scintillation crystals to which the second linear one-dimensional array of light sensors is coupled.

14. The apparatus of claim 13 further comprising:
a third linear one-dimensional array of light sensors coupled to a second row of scintillation crystals of the block, wherein the third linear array of light sensors is parallel to the first non-planar array of light sensors; and a fourth linear one-dimensional array of light sensors coupled a second column of scintillation crystals of the block, wherein the fourth linear array of light sensors is parallel to the second linear one-dimensional array of light sensors; and
the apparatus does not comprise light sensors in the Y-dimension between the first linear one-dimensional array of light sensors and the third linear one-dimensional array of light sensors; and
the apparatus does not comprise light sensors in the X-dimension between the second linear one-dimensional array of light sensors and the fourth linear one-dimensional array of light sensors.

15. The apparatus of claim 12 wherein:
the first portion of the reflecting film comprises a first plurality of openings; and
the second portion of the reflecting film comprises a second plurality of openings.

16. The apparatus of claim 15 wherein:
the first plurality of openings is configured to allow light to traverse between two channels to reach the closest neighboring sensors in the first linear one-dimensional array of light sensors; and
the second plurality of openings is configured to allow light to traverse between two channels to reach the closest neighboring sensors in the second linear one-dimensional array of light sensors.

17. The apparatus of claim 9 wherein the first and second linear one-dimensional arrays of light sensors comprise silicon photomultipliers.

18. An apparatus configured as positron emission detector, the apparatus comprising:
a block having X-Y-Z dimensions comprising scintillation crystals having a first end and a second end;
a first plurality of light sensors in a first X-Y plane coupled to the first end of the scintillation crystals;
a second plurality of light sensors in a second X-Y plane coupled to the second end of the scintillation crystals, wherein the second linear one-dimensional array of light sensors is spaced apart from the first linear one-dimensional array of light sensors in the Z-dimension, wherein
an X-Y location of a signal emitted by a scintillation crystal is determined by an X-Y location of a first sensor in the first plurality of sensors that detects the signal and by an X-Y location of a second sensor in the second plurality of sensors that detects the signal;
a Z-location of the signal is determined by a difference in signal intensities detected by the first sensor and the second sensor;
the first plurality of light sensors is a first linear one-dimensional array;
the second plurality of light sensors is a second linear one-dimensional array;
the apparatus does not comprise light sensors between the first plurality of light sensors in the first X-Y plane coupled to the first end of the scintillation crystals and the second plurality of light sensors in the second X-Y plane coupled to the second end of the scintillation crystals.

19. An apparatus configured as positron emission detector, the apparatus comprising:
a block comprising scintillation crystals comprising a first end and a second end;
reflective film coupled to the scintillation crystals;
a first plurality of light sensors coupled to the first end of the scintillation crystals; and a second plurality of light sensors coupled to the second end of the scintillation crystals, wherein:
the first plurality of light sensors comprises individual light sensors coupled to adjacent scintillation crystals in the block;
the second plurality of light sensors comprises individual light sensors coupled to adjacent scintillation crystals in the block;
an individual scintillation crystal in the block is coupled to no more than one individual light sensor in the first plurality of light sensors and no more than one individual light sensor in the second plurality of light sensors;
the first plurality of light sensors is a first linear one-dimensional array;
the second plurality of light sensors is a second linear one-dimensional array; and
the apparatus does not comprise light sensors in between the first plurality of light sensors coupled to the first end of the scintillation crystals and the second plurality of light sensors coupled to the second end of the scintillation crystals.

20. A method of detecting an X-Y-Z location of a scintillating crystal in a crystal block, the method comprising:
obtaining a first set X and Y coordinates for a first sensor that detects light from the scintillating crystal;
obtaining a second set of X and Y coordinates for a second sensor that detects light from the scintillating crystal;
determining an X coordinate and a Y coordinate of the scintillating crystal based on the first set of X and Y coordinates and the second set of X and Y coordinates;
determining a Z coordinate of the scintillating crystal based on the amount of light detected by the first sensor and the second sensor, wherein:
the first sensor is a sensor in a first linear one-dimensional array of light sensors; and
the second sensor is a sensor in a second linear one-dimensional array of light sensors, wherein the second linear one-dimensional array of light sensors is spaced apart from the first linear one-dimensional array of light sensors in the Z-dimension and there are no light sensors in the Z-dimension between the first linear one-dimensional array of light sensors and the second linear one-dimensional array of light sensors.

* * * * *